(12) United States Patent
Molnar

(10) Patent No.: US 9,918,618 B2
(45) Date of Patent: *Mar. 20, 2018

(54) MEDICAL DEVICES AND METHODS OF PLACEMENT

(71) Applicant: WM & DG, INC., Deerfield, IL (US)

(72) Inventor: Robert W. Molnar, Long Grove, IL (US)

(73) Assignee: WM & DG, Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/455,470

(22) Filed: Aug. 8, 2014

(65) Prior Publication Data

US 2016/0038008 A1    Feb. 11, 2016

(51) Int. Cl.
| | | |
|---|---|---|
| A61B 1/00 | (2006.01) | |
| A61B 1/07 | (2006.01) | |
| A61B 7/02 | (2006.01) | |
| A61B 1/233 | (2006.01) | |
| A61B 1/24 | (2006.01) | |

(Continued)

(52) U.S. Cl.
CPC ........ *A61B 1/00154* (2013.01); *A61B 1/0014* (2013.01); *A61B 1/00016* (2013.01); *A61B 1/00135* (2013.01); *A61B 1/00137* (2013.01); *A61B 1/00142* (2013.01); *A61B 1/05* (2013.01); *A61B 1/07* (2013.01); *A61B 1/233* (2013.01); *A61B 1/24* (2013.01); *A61B 1/2673* (2013.01); *A61B 1/303* (2013.01); *A61B 7/023* (2013.01); *A61M 16/0463* (2013.01); *A61M 16/0465* (2013.01); *A61M 16/0488* (2013.01); *A61M 16/0666* (2013.01); *A61B 1/00078* (2013.01); *A61B 1/015* (2013.01); *A61B 1/018* (2013.01); *A61B 5/0008* (2013.01); *A61B 5/01* (2013.01)

(58) Field of Classification Search
CPC ............ A61B 1/00009; A61B 1/00016; A61B 1/00114; A61B 1/00154; A61B 1/015
See application file for complete search history.

(56) References Cited

U.S. PATENT DOCUMENTS

| | | | |
|---|---|---|---|
| 4,231,365 | A | 11/1980 | Scarberry |
| 4,360,008 | A | 11/1982 | Corazzelli, Jr. |

(Continued)

FOREIGN PATENT DOCUMENTS

| | | |
|---|---|---|
| EP | 0 665 029 A2 | 8/1995 |
| KR | 2012-0095385 | 8/2012 |

(Continued)

OTHER PUBLICATIONS

Bledsoe, "The Disappearing Endotrachael Tube"., Clinical Professor of Emergency Medicine, University of Nevada School of Medicine.
"Incubation Threatened by New Devices and Lack of Paramedic Practice", Patient Care, Jems.com; http://www.jems.com/article/patient-care/incubation-threatened-new-devi.
"Incubation Threatened by New Devices and Lack of Paramedic Practice", Patient Care; http://www.jems.com/article/patient-care/intubation-threatened-new-devi.

(Continued)

*Primary Examiner* — Baisakhi Roy
(74) *Attorney, Agent, or Firm* — Greer, Burns & Crain, Ltd.

(57) ABSTRACT

The present invention provides improved medical devices equipped with a visualization device for intubation, ventilation, drug delivery, feeding and continuous remote monitoring of a patient. The present invention also provides methods for rapid and accurate placement of a medical device in a patient and continuous real time monitoring, including a remote monitoring, of the patient after the placement.

22 Claims, 30 Drawing Sheets

(51) Int. Cl.
  *A61B 1/267* (2006.01)
  *A61B 1/303* (2006.01)
  *A61M 16/04* (2006.01)
  *A61M 16/06* (2006.01)
  *A61B 1/05* (2006.01)
  A61B 1/015 (2006.01)
  A61B 1/018 (2006.01)
  A61B 5/01 (2006.01)
  A61B 5/00 (2006.01)

(56) References Cited

U.S. PATENT DOCUMENTS

| | | | |
|---|---|---|---|
| 4,577,638 A | 3/1986 | Graham | |
| 4,584,998 A | 4/1986 | McGrail | |
| 4,607,643 A | 8/1986 | Bell et al. | |
| 5,052,386 A | 10/1991 | Fischer, Jr. | |
| 5,193,692 A | 3/1993 | Farley et al. | |
| 5,241,956 A | 9/1993 | Brain | |
| 5,353,787 A | 10/1994 | Price | |
| 5,400,771 A | 3/1995 | Pirak et al. | |
| 5,499,625 A | 3/1996 | Frass et al. | |
| 5,511,916 A | 4/1996 | Farley et al. | |
| 5,513,627 A | 5/1996 | Flam | |
| 5,515,844 A * | 5/1996 | Christopher | A61M 16/10 128/200.26 |
| 5,551,947 A | 9/1996 | Kaali | |
| 5,632,271 A | 5/1997 | Brain | |
| 5,682,880 A | 11/1997 | Brain | |
| 5,733,242 A * | 3/1998 | Rayburn | A61B 1/0052 600/120 |
| 5,740,791 A | 4/1998 | Aves | |
| 5,819,733 A | 10/1998 | Bertram | |
| 5,879,306 A * | 3/1999 | Fontenot | A61B 5/0086 600/473 |
| 5,888,195 A | 3/1999 | Schneider | |
| 6,142,144 A | 11/2000 | Pacey | |
| 6,189,533 B1 | 2/2001 | Simon et al. | |
| 6,196,225 B1 | 3/2001 | Allgeyer | |
| 6,349,720 B1 | 2/2002 | Clark | |
| 6,386,199 B1 | 5/2002 | Alfery | |
| 6,439,232 B1 | 8/2002 | Brain | |
| 6,440,061 B1 | 8/2002 | Wenner et al. | |
| 6,443,156 B1 | 9/2002 | Niklason et al. | |
| 6,527,704 B1 | 3/2003 | Chang et al. | |
| 6,543,447 B2 * | 4/2003 | Pacey | A61B 1/05 128/200.26 |
| 6,626,169 B2 | 9/2003 | Gaitini | |
| 6,631,720 B1 | 10/2003 | Brain | |
| 6,634,354 B2 | 10/2003 | Christopher | |
| 6,655,377 B2 * | 12/2003 | Pacey | A61B 1/2676 128/200.26 |
| 6,860,264 B2 | 3/2005 | Christopher | |
| 6,860,270 B2 | 3/2005 | Sniadach | |
| 6,918,391 B1 | 7/2005 | Moore | |
| 7,052,456 B2 | 5/2006 | Simon | |
| 7,128,509 B2 | 10/2006 | Farley et al. | |
| 7,156,091 B2 | 1/2007 | Koyama et al. | |
| 7,237,993 B2 | 7/2007 | Farley et al. | |
| 7,331,925 B2 | 2/2008 | McMorrow et al. | |
| 7,421,877 B2 | 9/2008 | Frenken | |
| 7,450,746 B2 | 11/2008 | Yang et al. | |
| 7,520,857 B2 | 4/2009 | Chalana et al. | |
| 7,527,601 B2 | 5/2009 | Dubey et al. | |
| 7,611,466 B2 | 11/2009 | Chalana et al. | |
| 7,654,970 B2 | 2/2010 | Dubey | |
| 7,713,189 B2 | 5/2010 | Hanke | |
| 7,713,216 B2 | 5/2010 | Dubey et al. | |
| 7,727,150 B2 | 6/2010 | Chalana et al. | |
| 7,744,534 B2 | 6/2010 | Chalana et al. | |
| 7,749,165 B2 | 7/2010 | McMorrow et al. | |
| 7,749,176 B2 | 7/2010 | Dubey | |
| 7,811,239 B2 | 10/2010 | Dubey et al. | |
| 7,819,806 B2 | 10/2010 | Yang et al. | |
| 7,854,324 B2 | 12/2010 | Farley et al. | |
| 7,896,007 B2 | 3/2011 | Brain | |
| 7,921,847 B2 | 4/2011 | Totz | |
| 7,942,813 B2 | 5/2011 | Mackin | |
| 7,976,458 B2 | 7/2011 | Stefanchik et al. | |
| 8,016,760 B2 | 9/2011 | Chalana et al. | |
| 8,038,629 B2 | 10/2011 | Solanki et al. | |
| 8,202,215 B2 | 6/2012 | Xiao et al. | |
| 8,215,307 B2 | 7/2012 | Nasir | |
| 8,297,275 B2 | 10/2012 | Ogilvie et al. | |
| 8,308,644 B2 | 11/2012 | McMorrow et al. | |
| 8,371,303 B2 | 2/2013 | Schaner et al. | |
| 8,529,442 B2 * | 9/2013 | Pacey | A61B 1/00142 600/187 |
| 8,928,746 B1 * | 1/2015 | Stevrin | G02B 23/2461 348/68 |
| 9,211,060 B2 | 12/2015 | Waldron et al. | |
| 9,415,179 B2 * | 8/2016 | Molnar | A61B 7/003 |
| 9,427,142 B2 | 8/2016 | Terliuc | |
| 9,579,012 B2 | 2/2017 | Vazales et al. | |
| 2003/0220542 A1 | 11/2003 | Belson et al. | |
| 2005/0182297 A1 | 8/2005 | Gravenstein et al. | |
| 2006/0111633 A1 | 5/2006 | McMorrow et al. | |
| 2006/0149129 A1 | 7/2006 | Watts et al. | |
| 2006/0162730 A1 | 7/2006 | Glassenberg et al. | |
| 2006/0180155 A1 | 8/2006 | Glassenberg et al. | |
| 2006/0276694 A1 | 12/2006 | Acha Gandarias | |
| 2007/0137651 A1 | 6/2007 | Glassenberg et al. | |
| 2007/0156068 A1 | 7/2007 | Dubey | |
| 2007/0180887 A1 | 8/2007 | Frenken | |
| 2007/0203393 A1 | 8/2007 | Stefanchik | |
| 2007/0239197 A1 | 10/2007 | Dubey | |
| 2007/0255185 A1 | 11/2007 | Dubey | |
| 2008/0029100 A1 | 2/2008 | Glassenberg et al. | |
| 2008/0114268 A1 | 5/2008 | Dubey | |
| 2008/0146879 A1 * | 6/2008 | Pacey | A61B 1/05 600/188 |
| 2008/0188774 A1 | 8/2008 | Dubey | |
| 2008/0276932 A1 | 11/2008 | Bassoul | |
| 2009/0194114 A1 | 8/2009 | Chen et al. | |
| 2009/0227835 A1 | 9/2009 | Terliuc | |
| 2010/0051024 A1 * | 3/2010 | Abrons | A61M 16/0488 128/200.26 |
| 2010/0113916 A1 | 5/2010 | Kumar | |
| 2010/0249639 A1 | 9/2010 | Bhatt | |
| 2010/0261967 A1 | 10/2010 | Pacey et al. | |
| 2010/0312069 A1 * | 12/2010 | Sutherland | A61B 17/0218 600/245 |
| 2011/0030694 A1 | 2/2011 | Schaner et al. | |
| 2011/0178372 A1 | 7/2011 | Pacey et al. | |
| 2011/0201882 A1 | 8/2011 | Schwartz et al. | |
| 2011/0315147 A1 | 12/2011 | Wood et al. | |
| 2012/0059223 A1 * | 3/2012 | McGrath | A61B 1/267 600/185 |
| 2012/0259173 A1 * | 10/2012 | Waldron | A61B 1/00073 600/109 |
| 2012/0260921 A1 | 10/2012 | Sangwan | |
| 2012/0302833 A1 | 11/2012 | Hayman et al. | |
| 2013/0006051 A1 | 1/2013 | Stace et al. | |
| 2013/0030249 A1 | 1/2013 | Vazales et al. | |
| 2013/0197303 A1 * | 8/2013 | Chun | A61M 16/06 600/103 |
| 2013/0253368 A1 | 9/2013 | Are et al. | |
| 2013/0324798 A1 | 12/2013 | Molnar et al. | |
| 2014/0018626 A1 | 1/2014 | Lee | |
| 2014/0166020 A1 | 6/2014 | Chang | |
| 2014/0194694 A1 | 7/2014 | Chen | |
| 2014/0357951 A1 * | 12/2014 | Muller | G02B 23/2415 600/111 |
| 2016/0038014 A1 | 2/2016 | Molnar | |

FOREIGN PATENT DOCUMENTS

| | | |
|---|---|---|
| WO | 94/05200 | 3/1994 |
| WO | 03/084719 A2 | 10/2003 |
| WO | WO 2008/123934 A1 | 10/2008 |
| WO | 2009025843 A1 | 2/2009 |
| WO | 2010/120950 | 10/2010 |

(56) References Cited

FOREIGN PATENT DOCUMENTS

| WO | 2012/080293 A2 | 6/2012 |
| WO | 2013/017535 A2 | 2/2013 |
| WO | WO2015013172 A2 | 1/2015 |

OTHER PUBLICATIONS

"Continuous Airway Control"; Vivasight.
Genzwuerker, MD. et al. "Laryngeal tube: a review of current literature" AJA-Online.com 2011:vol. 12.
Kidali MD, "Capnography in emergency medicine—911" http://www.capnography.com/outside/922.htm.
VivaSight, Airway management for lung isolation, ETVIEW.
ETView Medical, Ltd., Announces Exclusive Patent License Agreement—Feb. 22, 2012. ETVIEW.
ETVIEW, http://www.etview.com/index_old.php.
VivaSight-SL, ETVIEW.
How to Use a Jem Endotrachael Tube Changer.
ETView Medical, Ltd., Announces Exclusive Patent License Agreement—Feb. 2, 2012, http://worldnetdaily.com.uk/markets/news/read/20671060/etview_medical, Jul. 5, 2012.
ETView Medical, Ltd., Announces the Appointment of David Amar, MD to Its Scientific Advisory Board, 2012; http://finance.yahoo.com/news/etview-medical-ltd-announces-appointment-104300770.html, Jun. 4, 2012, 3 pages.

\* cited by examiner

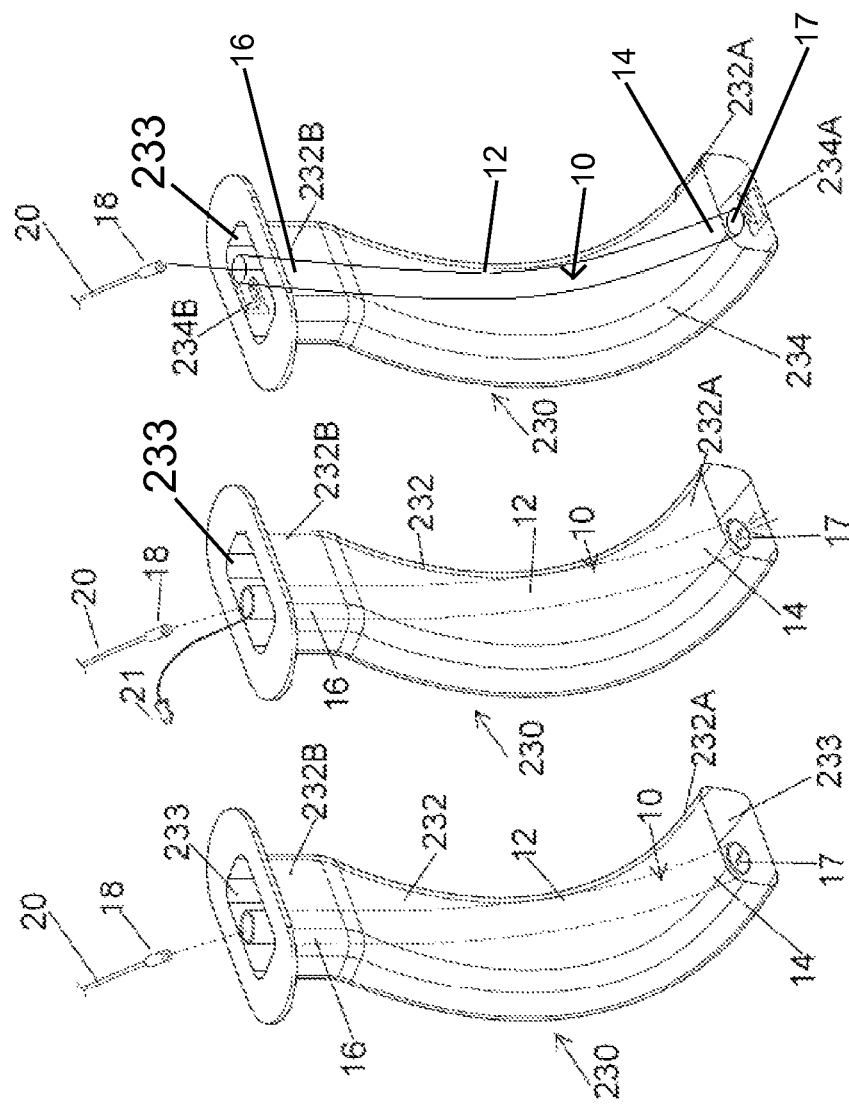

MEDICAL DEVICES AND METHODS OF PLACEMENT

FIELD OF THE INVENTION

The invention provides various medical devices, each with a camera placed in a camera tube, which allows for one camera to provide continuous visualization for each device during and after placement in a patient. A sound device, such as a microphone, is incorporated in many devices and provides continuous monitoring of breath and heart sounds in a patient. The camera and microphone do not contact the patient's tissues and thus, do not require sterilization. The continuous visualization and sound monitoring of the patient are in real time and enable remote monitoring as well. Methods for rapid and accurate placement of a medical device in a patient are provided as well.

BACKGROUND

Various devices are available to stabilize a patient and facilitate his breathing, feeding and medication delivery. Such devices are used in patients during surgical procedures, after certain traumas including spinal cord injuries, and in patients suffering from certain medical conditions including advanced Alzheimer disease. These devices include endotracheal tubes, airway devices, feeding tubes, oral airways, nasal cannulas and the like.

Because human anatomy varies significantly from a patient to a patient, properly placing a medical device in a patient's trachea requires a significant skill and is a task laced with inherent risk. The task becomes even more complicated because the insertion procedure may have to be performed immediately at an accident site, on pediatric patients, in a nursing home, on a battlefield or at a natural disaster site where many patients have to be attended at the same time.

The process of placing a breathing tube in a patient is called intubation. Devices such as laryngoscopes, videolaryngoscopes, fiberoptic scopes, as well as other proprietary videoscopes have been developed. These devices provide accuracy for initial placement, but do not provide continuous visualization or mobility of the image after a medical device has been placed in a patient. Newer devices, such as Vivasight SL or DL endotracheal tubes, provide continuous visualization, but are costly because they depend on a single use of disposable cameras and they are not transferrable from one medical device to another. The Totaltrack VLM supraglottic airway has a proprietary reusable camera for only its one device, and it cannot be transferred to other medical devices.

Thus, there remains the need for improved devices which can be easily monitored remotely by a qualified personal during placement and after placement for an adverse reaction. After a medical device has been placed in a patient, the need remains to monitor in real time the patient's possible adverse reactions such as for example, aspiration, airway secretion, apnea, etc.

SUMMARY OF THE INVENTION

At least some of these needs are addressed by present medical devices which are equipped with a portable universal visualization device in which a camera is contained within a separate camera tube and which transmits information that can be accessed and monitored remotely and simultaneously from several patients in real time.

One embodiment provides a medical visualization device which comprises a camera tube with a distal end and a proximal end. The distal end is sealed with a transparent material and a proximal end has an opening. A camera with a wire is placed inside of the camera tube. The camera can be placed inside of the camera tube and it can be retracted from the camera tube on demand. The camera can be reused in various devices without sterilization. The camera can transmit images to a remote location wirelessly. In some embodiments, the camera tube comprises a fiber optic material. The visualization device can be equipped with at least one of the following: a light source, a stylet, a bougie and a sound- and temperature-monitoring device which can transmit the information to a remote location wirelessly. The visualization device can transmit images, sounds and other data to any number of remotely located monitoring devices and/or data storage devices. Such devices include, but are not limited to, a wireless portable device, smart phone, tablet, watch, cell phone, hand-held wireless device, computer, remote data server, radio, television, walkie-talkie and the like.

A further embodiment provides a method of continuous monitoring of a patient's at least one internal organ, the method comprising placing in the patient the visualization device with the camera in the sealed camera tube, causing the camera to transmit images of the internal organ in real time through the transparent material at the distal end of the camera tube, and analyzing the transmitted images. In some embodiments, the images are transmitted wirelessly to at least one remote location.

Various internal organs can be monitored by this method, including nasopharynx, pharynx, hypopharynx, supraglottic structures, airway, trachea, vocal cords, stomach, and vagina.

In some embodiments, the length of the camera tube in the visualization device is adjustable and it can be adjusted to the length of at least one of the following devices: an endotracheal tube, a supraglottic airway, airway device, oral airway, dilator, tracheostomy device, intubating oral airway, esophageal stethoscope, nasal cannula, feeding tube, suction tube and endotracheal changing tube.

Further embodiments provide a method for placing a medical device in a patient in which the medical device is equipped with the visualization device and a bougie. The medical device is inserted in the patient and the placement of the device is guided with the bougie under continuous visualization.

A kit for monitoring a patient's internal organ in real time is also provided. The kit comprises a camera tube with the adjustable length and with at least one ring attached externally to the camera tube, wherein the camera tube has a distal end and a proximal end and wherein the distal end of the camera tube is sealed with a transparent material; and a reusable camera which can be placed and removed from the camera tube and which can transmit images wirelessly to at least one remote location. This real time information obtained with the visualization device can be transferred or stored to multiple distant monitoring sites.

Also provided is a medical device comprising a visualization device sealed to, attached to or otherwise combined with at least one of the following second devices: an endotracheal tube, a supraglottic airway device, a ventilator adaptive cap, a dilator, a tracheostomy device, a nasal trumpet, a an oral airway, an esophageal stethoscope, a laryngoscope, a speculum, a nasal cannula, a feeding tube, a suction tube, a suction catheter, and an endotracheal changing tube; and wherein the visualization device comprises a camera tube with a distal end and proximal end, the distal end being sealed with a transparent material and a camera being placed inside of the camera tube through an opening at the proximal end. These medical devices can be further equipped with at least one of the following a bougie, a flexible stylet and a sound- and temperature-monitoring device. In some embodiments, the visualization device is sealed, attached or otherwise connected externally to the second device. In other embodiments, the visualization device can be placed inside of the second device. Various endotracheal tubes equipped with the visualization device are contemplated as well, including an endotracheal tube which comprises a sleeve through which the visualization device can be inserted, an endotracheal tube into which the visualization device is placed internally through a ventilator adaptive cap and an endotracheal tube to which the visualization device is attached externally.

BRIEF DESCRIPTION OF THE DRAWINGS

FIG. 4A is an embodiment without a light source and FIG. 4B is an embodiment with a light source.

FIG. 9A is a side view of a visualization device equipped with two rings. FIG. 9B is a side view of the visualization device as shown in FIG. 9A, but equipped further with a bougie. FIG. 9C is a side view of the visualization device as shown in FIG. 9A, but equipped further with a light source.

FIG. 11A is a side view of the airway device and FIG. 11B is the device as shown in FIG. 11A, but with a ventilator adaptive cap.

FIG. 12A is a side view of the oral airway device, while FIGS. 12B and 12C are cross-sections through the airway device in its full cylinder form (FIG. 12B) and in its half-cylinder form in which one half-cylinder is retracted into the other half-cylinder (FIG. 12C).

FIG. 14A depicts an embodiment in which the visualization device is attached externally to a tracheostomy tube, while FIG. 14B depicts an embodiment in which the visualization device is attached inside of the tracheostomy tube.

FIGS. 16A-16C depict a side view of an oral airway equipped with a visualization device and FIG. 16D depicts an intubating oral airway also equipped with a visualization device. FIG. 16A shows a visualization device being positioned inside of the oral airway. FIG. 16B is the same as FIG. 16A, but includes a light source for the visualization device. FIG. 16C is the same as FIG. 16A, but includes a whistle. FIG. 16D is an intubating oral airway with a main lumen into which an endotracheal tube can be placed.

FIG. 18A shows a laryngoscope with a visualization device, and FIG. 18B is the same, except it is further equipped with a bougie and the visualization device is equipped with a light source.

FIG. 20A depict positioning of the cannula on a patient's head and FIG. 20B is the same as in FIG. 20A, except the visualization device is equipped with a light source. FIG. 20C is a side view of the cannula of FIG. 20A, and FIG. 20D is a side view of the cannula of FIG. 20B. FIG. 20E is a cross-sectional view of a patient's head with the cannula of FIG. 20A inserted. FIG. 20F is a further embodiment in which a nasal cannula with a visualization device as shown in FIG. 20A is further combined with an external stethoscope.

FIG. 22A depicts a visualization device positioned inside of the suction tube. FIG. 22B the same as in 22A, but equipped further with a bougie, and FIG. 22C is the same as FIG. 22B, but showing the bougie protruding from the distal end of the suction tube.

DETAILED DESCRIPTION

The present invention provides improved medical devices equipped with a visualization device for intubation, ventilation, feeding and monitoring of a patient. The present invention also provides methods for rapid and accurate placement of a medical device in a patient and remote continuous real-time monitoring of the patient after the placement.

These medical devices are equipped with a visualization device in which a camera is placed in a separate sealed camera tube. As the camera does not come in contact with a patient, there is no need to sterilize the camera and the same camera can be reused in many applications. Thus, the same camera can be switched between different medical devices which monitor internal organs such as medical devices that are placed in patient's airway, larynx, gastrointestinal tract, chest or vaginal cavity.

Figure 1A:
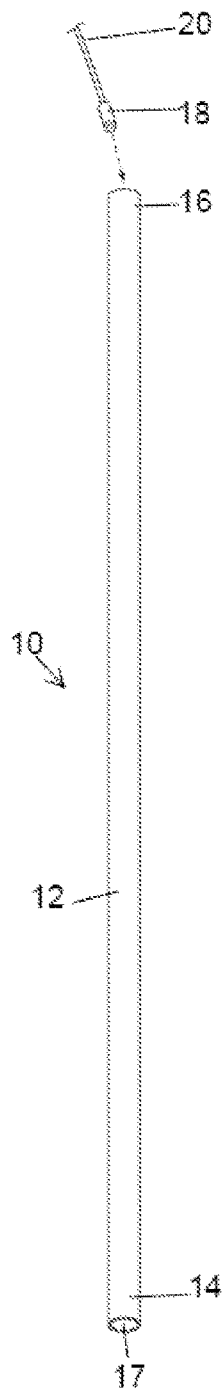
FIGS. 1A, 1B and 1C depict a side view of an embodiment for a visualization device as shown in FIG. 1A which can be further equipped with a stylet as shown in FIGS. 1B and 1C.
Figure 1B:
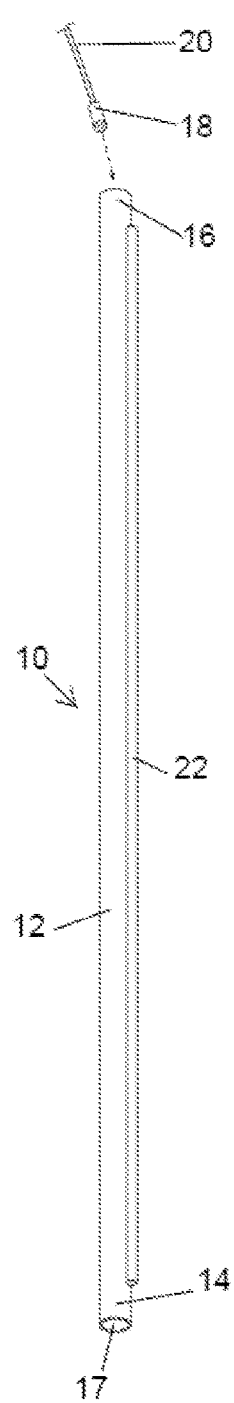
Figure 1C:
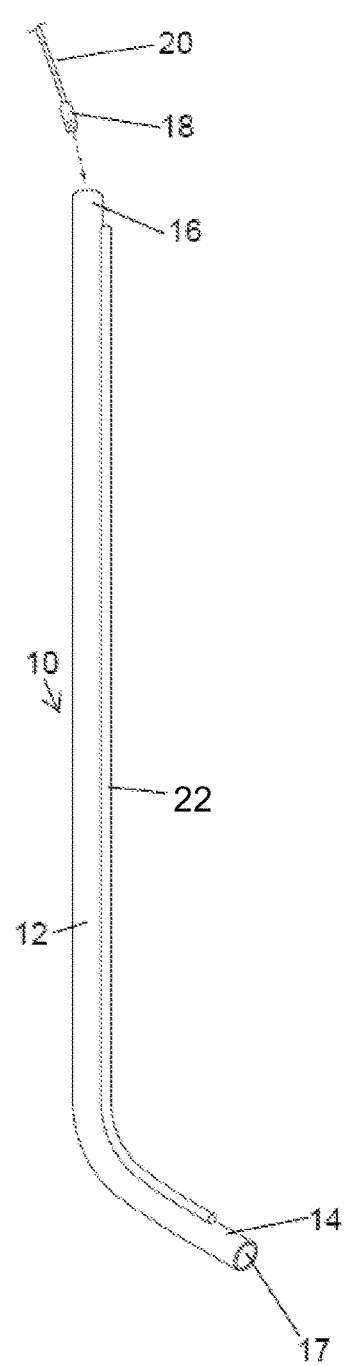

One embodiment provides a visualization device as shown in FIG. 1A and its further embodiments as shown in FIGS. 1B and 1C. A visualization device, generally 10, in FIG. 1A comprises a camera tube 12 with a distal end 14 and a proximal end 16. The camera tube 12 can be a plastic tubing. In some embodiments, the camera tube 12 may comprise a fiber-optic material. The camera tube 12 is sealed at the distal end 14 with a transparent material 17. The diameter of camera tube 12 is designed in such a way that a camera 18 with wire 20 can be inserted inside of the camera tube 12 through an opening at the proximal end 16 and moved down the camera tube 12 toward the distal end 14, so that the camera 18 transmits continuously images obtained through the transparent material 17. The length of the camera tube 12 can vary and it can be adjusted dependent on the length of a medical device with which the visualization device is to be used. For example, the length of the camera tube 12 may be longer when the visualization device 10 is used with a feeding tube in comparison to the length of the camera tube 12 when the visualization device 10 is used with an endotracheal tube. In some embodiments, the visualization device obtains images and transmits wirelessly, broadcasts or records this information to at least one device positioned at a remote location.

Because the camera tube 12 is sealed at the distal end 14 with the transparent material 17, the camera 18 does not come in contact with patient's tissues or fluids and therefore, the camera 18 does not have to be sterilized or to be disposable, and it can be reused in further applications. However, the camera 18 can be disposable in some applications. The camera 18 can be loaded with a chip and equipped to obtain and transmit digital images in real time. The camera 18 is further connected by an electric wire 20 to an image receiving and processing device (not shown) such as a computer equipped with a monitor or a computer network. The camera 18 may also be in communication wirelessly with an image-receiving device located at any location, including multiple locations and remote locations. Because the length and diameter of the camera tube 12 can be adjusted based on patient's needs, the visualization device 10 is suitable for a broad variety of patients, including pediatric patients and adult patients with abnormal anatomy or trauma.

As the visualization device 10 is bendable and flexible, the visualization device 10 is easy to insert in a patient and remove from the patient. The camera 18 may have its own light source. As the visualization device 10 transmits images from a patient in real time, it can be used for guiding a medical device for proper placement. Thus, some embodiments are concerned with methods for rapid and accurate placement of a medical device inside of a patient, including a method for guided and rapid placement into patient's airway, larynx, gastrointestinal tract, chest or vaginal cavity under continuous visualization.

As shown in embodiment of FIG. 1B, the visualization device 10 can be further equipped with a stylet 22 which can be sealed onto or otherwise attached to the camera tube 12 externally on at least one side of the camera tube 12 along the proximal-to-distal (16-14) axis of the camera tube 12. The stylet 22 can be made of metal wire or some other sturdy material with the purpose to keep the otherwise flexible visualization device 10 in a particular shape. In some embodiments, the stylet 22 can be of the same length as the camera tube 12. In other embodiments, the stylet 22 is shorter than the camera tube 12 such that at a least a portion of the camera tube 12 on either the proximal end 16 or distal end 14, or on the both ends 16 and 14 is not in contact with the stylet 22. As shown in FIG. 1C, the stylet 22 can be bent into various shapes and it retains the shape into which it has been bent, which permits for visualization device 10, which is otherwise flexible, to retain a particular shape.

In alternative embodiments, the visualization device 10 can be equipped with a bougie which can be attached to the camera tube 12 externally on at least one side of the camera lumen 12 along the proximal-distal (16-14) axis of the visualization device 10.

The bougie can be made of various materials, including plastic material which is bendable. As the bougie is bendable, but keeps a shape into which it is bent, the bougie is suitable for guiding the visualization device 10 inside of a patient. In some embodiments, the bougie can be of the same length as the camera tube 12. In other embodiments, the bougie can be made shorter or longer than the camera tube 12 such that only a portion of the camera tube 12 is in contact with the bougie. In some embodiments, the bougie protrudes on at least the distal end 14.

The visualization device 10 can be further equipped with a portable light source (not shown) which can be either built-in the camera 18 or it can be built-in the camera tube 12. In alternative, a light source can remain outside the camera tube 12 on the proximal end 16, but still be placed such that the light source sheds light inside of the camera tube 12.

In embodiments of FIGS. 1A-1C, the camera tube 12 can be disposable, while the camera 18 is reusable without the need of sterilization. However, the camera 18 can be also disposable in at least some embodiments.

During placement in a patient, a visualization device 10 either alone or in combination with another medical device is positioned such that it is inserted with its distal end 14 in the patient under continuous visualization with the camera 18.

Any of the visualization devices 10 described above can be attached, sealed or otherwise connected to a disposable or non-disposable medical device either externally or internally and as described in more detail below. Various medical devices for pediatric and adult patients can be built such that the camera device tube 12 is sealed or attached to the medical device during manufacturing.

In other embodiments, the visualization device 10 can be sold as a kit which can be attached by a medical practitioner to a pre-made medical device for pediatric and adult patients, based on a particular patient's individual needs. The length of the camera tube 12 can vary such that the camera tube 12 is of the same or similar length with a medical device to which the visualization device 10 is sealed, attached or otherwise connected to.

Having the ability to verify placement for a medical device in real time from near and far allows several experts to assist and verify placement. This is accomplished by equipping the medical device with the visualization device 10. In some embodiments, a method is provided in which the visualization device 10 is used for placing a medical device in a patient in ambulances, on battlefields, in nursing homes or hospitals. The visualization device 10 provides the ability to monitor in real time a patient. Because the visualization device 10 may interact with a plethora of devices disposable and otherwise, the use of the device 10 on various medical devices provides for a method in which a medical practitioner can customize a proper device for each patient or situation. Having the same camera equipment that can interact with various medical devices provides economy of scale such that even the smallest of organizations can have all the proper vigilance and technology.

At least in some embodiments the visualization device 10 can be used in assembly with at least one medical device as described in more detail below. A method in which the visualization device 10 is used on an airway device allows continuous visualization of any of the following in a patient in real time: nasopharynx, pharynx/hypo pharynx, supraglottic structures, airway, internal organ anatomy, vocal cords during normal and abnormal ventilation. This method also allows detection of abnormal anatomy and abnormal vocal cord movements.

Figure 2:
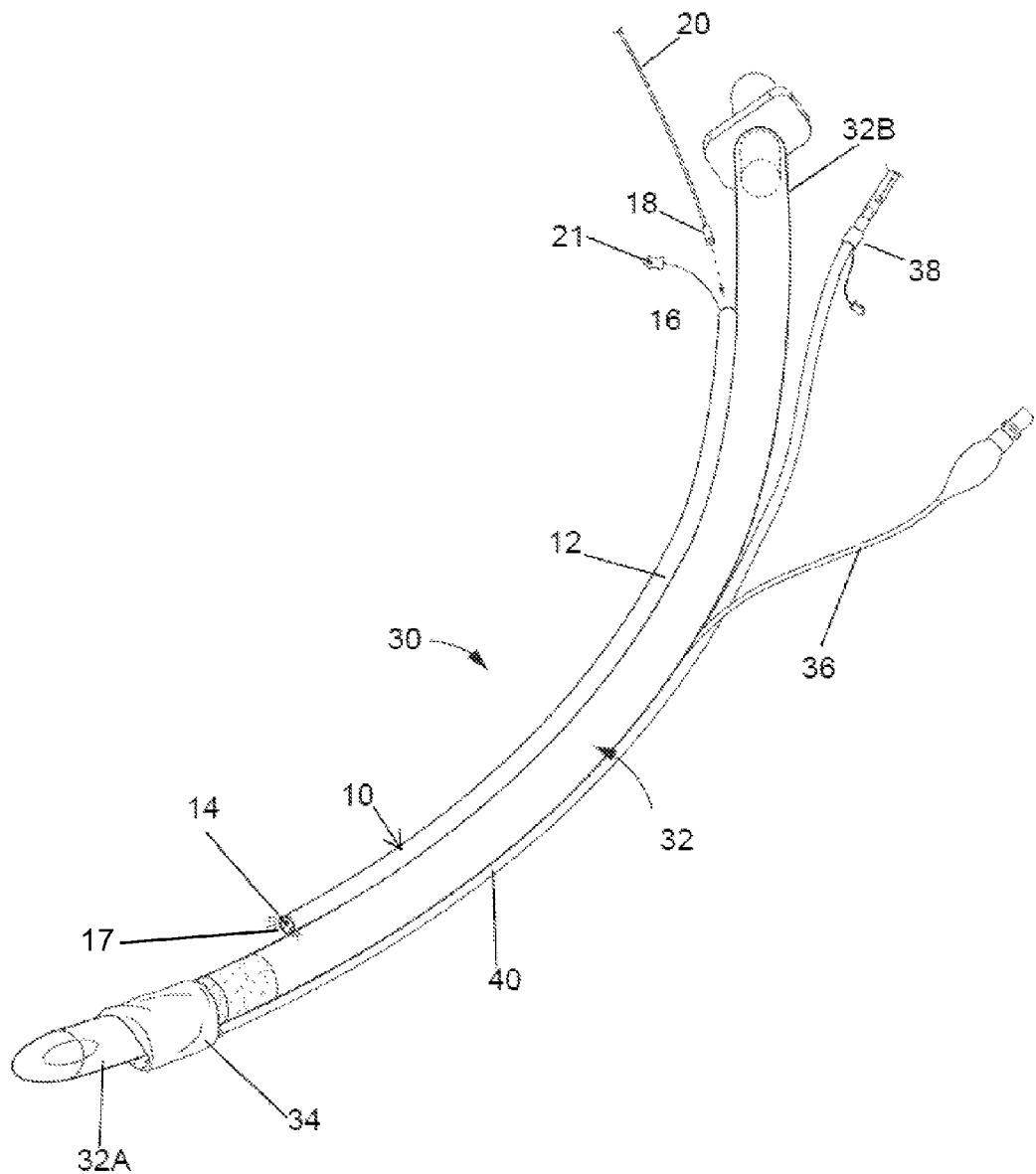
FIG. 2 depicts a side view of an embodiment for an endotracheal device equipped with a visualization device.

Referring to FIG. 2, this embodiment provides an endotracheal device, generally 30. The endotracheal device 30 comprises an endotracheal tube 32 with a distal end 32A and a proximal end 32B. The visualization device 10 is sealed or otherwise attached externally on at least one side of the endotracheal tube 32, along the proximal-distal (32B-32A) axis of the endotracheal tube 32. The visualization device 10 comprises essentially of all elements as shown in FIG. 1A, with the camera 18 inserted inside of the camera tube 12 through an opening at the proximal end 16 of the camera tube 12, all the way down to the distal end 14 and the opening of the distal end 14 being sealed with the transparent material 17. Because the camera 18 is positioned inside of the sealed camera tube 12, the camera 18 does not come into contact with a patient and the camera 18 does not need to be sterilized and can be reused in multiple applications. Thus, the camera 12 does not have to be disposable or to be sterilized before further applications. However, the camera 18 can be disposable in at least some applications.

As the camera 18 is contained inside of the separate camera tube 12 which is positioned externally on the endotracheal tube 32, a diameter of the camera tube 12 is not limited by a diameter of the endotracheal tube 32. Thus, the diameter of the camera tube 12 can be larger or smaller than the diameter of the endotracheal tube 32.

Thus, the visualization device 10 can be used on endotracheal devices for pediatric patients and patients with abnormal anatomy. In some embodiments, the visualization device 10 has a diameter larger than that of the endotracheal tube 32.

The camera 18 is connected by electric wire 20 to an external device such as a computer and monitor (not shown). At least in some embodiments, the visualization device 10 is further equipped with a light source 21. The light source 21 can be kept outside of the camera tube 12, but in proximity with the proximal end 16 of the visualization tube 12 so that the light source 21 sheds light inside of the camera tube 12. In alternative embodiments, the light source 21 can be built-in the camera tube 12 or in further embodiments, the light source 21 can be built-in the camera 18.

At least in some applications, the camera 18 is a digital camera equipped with a chip and it collects and transmits images continuously. The camera 18 can be connected wirelessly or hard-wired with a computer network (not shown) which collects and analyzes images obtained by the camera 18. This arrangement permits for remote, continuous and real time monitoring of the endotracheal device 30 during placement and after-placement in a patient. Thus, an accurate and rapid placement of the endotracheal device 30 can be achieved. Further and because the visualization device 10 continues to acquire images after the endotracheal device 30 is placed inside of a patient, the patient can be monitored in real time for adverse reactions such as bleeding, airway obstruction, shifting or malfunctioning, etc. of the endotracheal device 30 and other reactions. The endotracheal device 30 may continue to transmit images and information for as long as it remains in a patient.

In some embodiments, the endotracheal tube 32 is further fitted with a cuff 34 at its distal end 32A. In other embodiments, the endotracheal tube 32 is not fitted with the cuff 34. The cuff 34 can be inflated with a device 36 after the endotracheal device 30 is placed in a patient and its proper positioning inside of the patient is verified by images obtained with the visualization device 10.

The endotracheal device 30 can be further equipped with a sound-monitoring device 38 which is sealed onto or otherwise attached externally on one side of the endotracheal tube 32 along the proximal-distal axis (32B-32A) of the endotracheal tube 32. The sound-monitoring device 38 can be a microphone placed inside of a plastic tube 40. It monitors heart beats and breathing tones and can be connected by wire or wirelessly to a remote device which collects and monitors patient's vital signals. In the embodiment of FIG. 2, the visualization device 10 is placed proximally to the cuff 34 and externally to the endotracheal tube 32. It will be understood that the endotracheal device 30 can be built with any endotracheal tube 32, including single-lumen and double-lumen tubes. The endotracheal device 30 can be used for either pediatric or adult patients. The endotracheal device 30 can be made in various sizes.

Figure 3:
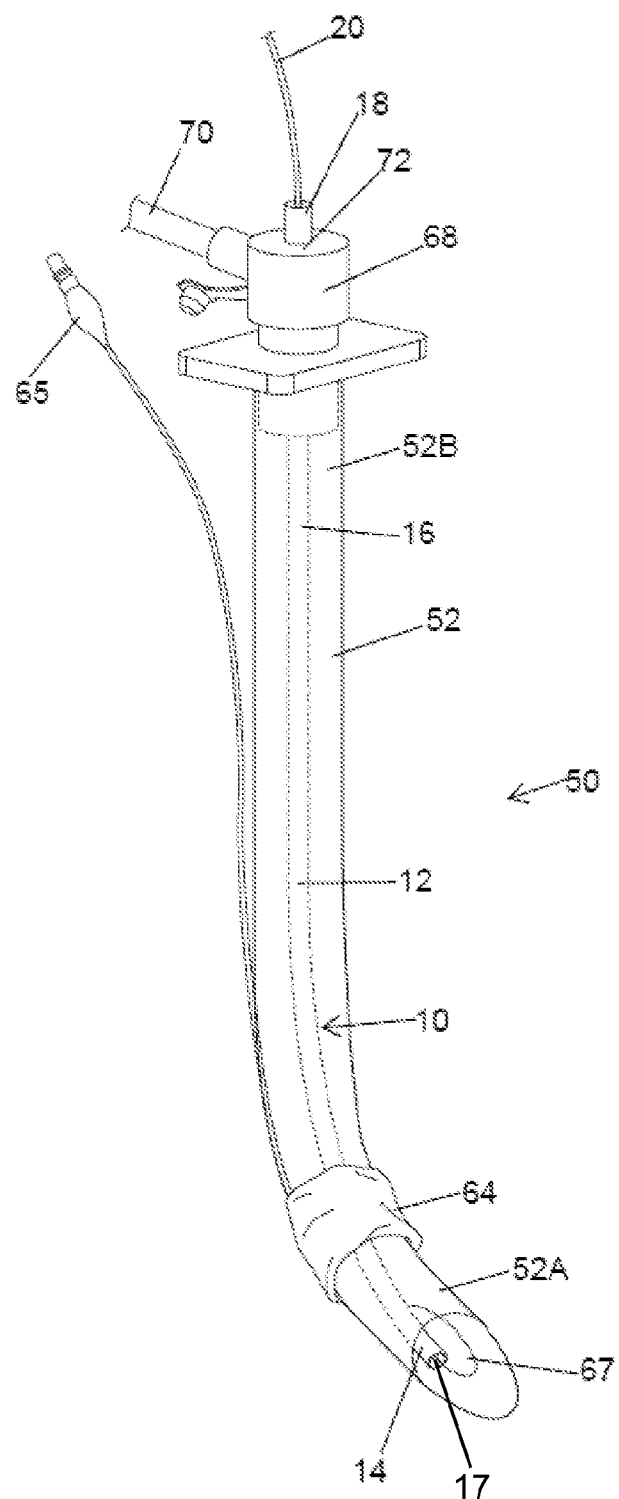
FIG. 3 depicts a side view of an alternative embodiment for an endotracheal device equipped with a visualization device.

In another embodiment and as shown in FIG. 3, an endotracheal device, generally 50, comprises an endotracheal tube 52 with a distal end 52A and a proximal end 52B, and a visualization device 10 placed inside of the endotracheal tube 52 through an opening in the proximal end 52B. In this embodiment, the visualization device 10 is attached to a built-in ventilator adaptable cap 68 which connects the endotracheal device 50 to a ventilator (not shown) through an outlet 70. The built-in ventilator adaptable cap 68 comprises an opening 72 through the cap 68. The visualization device 10 is passed through the opening 72 and is placed inside of the endotracheal tube 52. The built-in ventilator adaptable cap 68 is then connected with the endotracheal tube 52 at the proximal end 52B of the endotracheal tube 52.

The visualization device 10 is the same as the visualization device 10 of FIG. 1A and it comprises a camera tube 12 with a sealed distal end 14 and an open proximal end 16. A camera 18 is placed inside of the camera tube 12 through the proximal end 16 of the camera tube 12. The camera 18 is connected by electrical wire 20 to an image-monitoring device (not shown). In some embodiments, the camera 18 is connected wireless to an image-monitoring device (not shown). The camera 18 collects images continuously and in real time through a transparent material 17 with which the distal end 14 of the camera tube 12 is sealed. The images can be transmitted to a remote location.

The endotracheal tube 52 can be optionally equipped with a cuff 64 at the distal end 52A such that the cuff 64 wraps around the endotracheal tube 52 and the cuff 64 can be inflated with a device 65, once the endotracheal device 50 is properly placed inside of a patient's airway. As can be seen from FIG. 3, the distal end 14 of the visualization device 10 extends distally from the distal end 52A of the endotracheal tube 52 and below the cuff 64 such that even when the cuff 64 is inflated with a device 65 after placement in a patient, the visualization device 10 can still record images inside of a patient's body and below the cuff 64. Further, the endotracheal device 50 may have an elliptical opening 67 at the distal end 52A and the visualization device 10 can be positioned inside of the endotracheal tube 52 such that the distal end 14 of the visualization device 10 aligns with or is in close proximity with the elliptical opening 67 of the endotracheal tube 52.

Figure 4A:
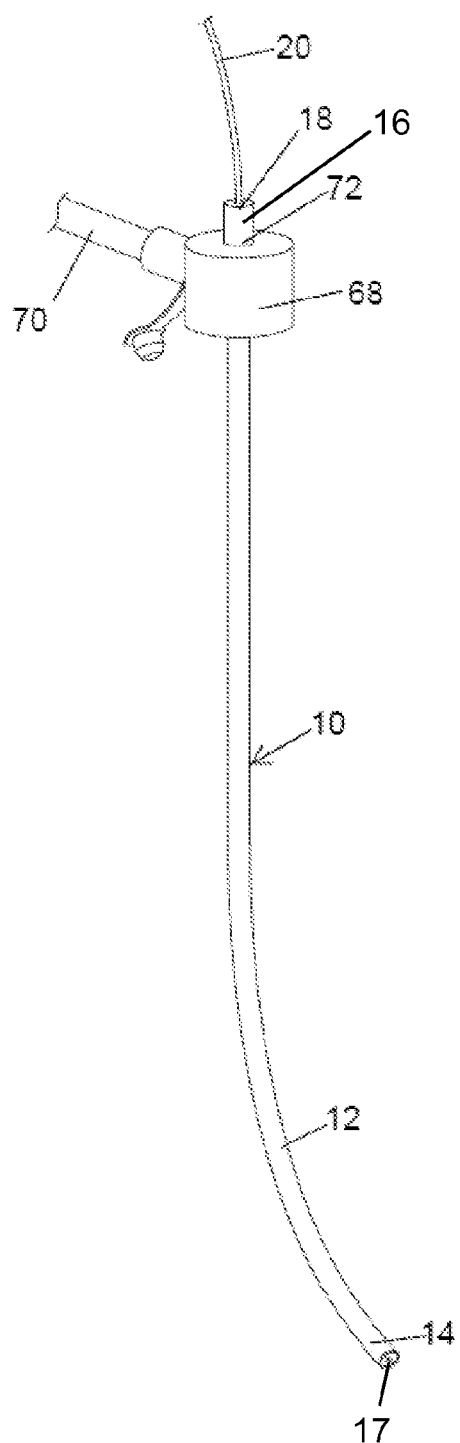
FIGS. 4A and 4B depict two embodiments showing a visualization device attached to a built-in ventilator adaptive cap.
Figure 4B:
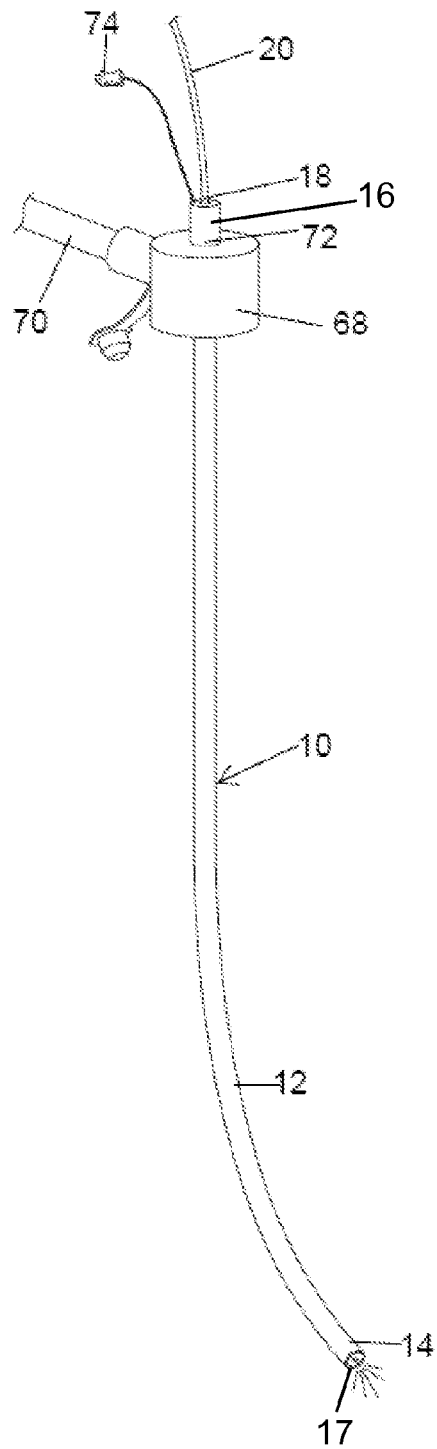

Referring to FIGS. 4A and 4B, further embodiments provide a visualization device 10 assembled with a built-in ventilator adaptable cap 68 which connects to a ventilator (not shown) by an outlet 70. The visualization device 10 is inserted through an opening 72 in the built-in ventilator adaptable cap 68 as shown in FIGS. 4A and 4B. As shown in FIG. 4B, the visualization device 10 can be further equipped with a light source 74 which can be a part of the camera tube 12 or it can be built in the camera 18, or it can remain outside the built-in ventilator adaptable cap 68. The visualization device 10 is assembled with the built-in ventilator adaptable cap 68 as shown in FIGS. 4A and 4B and can be then used in an endotracheal tube as described in connection with FIG. 3 or in a supraglottic device or with a laryngeal mask or with any other medical device to which a built-in ventilator adaptable cap 68 can be attached. As shown in FIGS. 4A and 4B, the camera tube 12 has a distal end 14 and a proximal end 16. The camera 18 is placed inside of the tube 12 through an opening in the proximal end 16 and moved all the way down to the distal end 14 which is sealed with a transparent material 17. The camera 18 collects images through the transparent material 17 and transmits the images in real time to a monitoring device which can be located remotely.

Figure 5A:
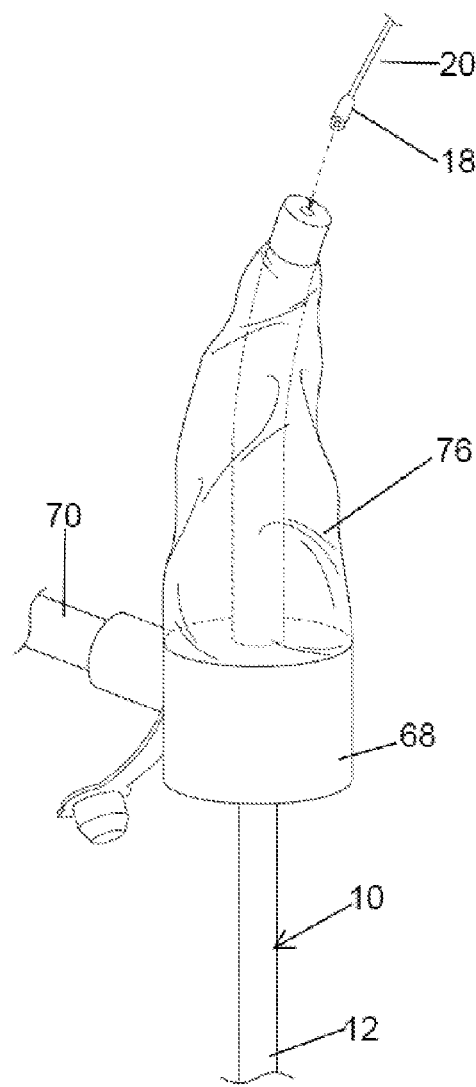
FIGS. 5A, 5B and 5C depict side views of further embodiments of a visualization device attached to a built-in ventilator adaptive cap and delivered through a sliding sleeve (FIGS. 5A and 5B), with further embodiment in FIG. 5C which includes a bougie or a flexible stylet as shown in the insert.
Figure 5B:
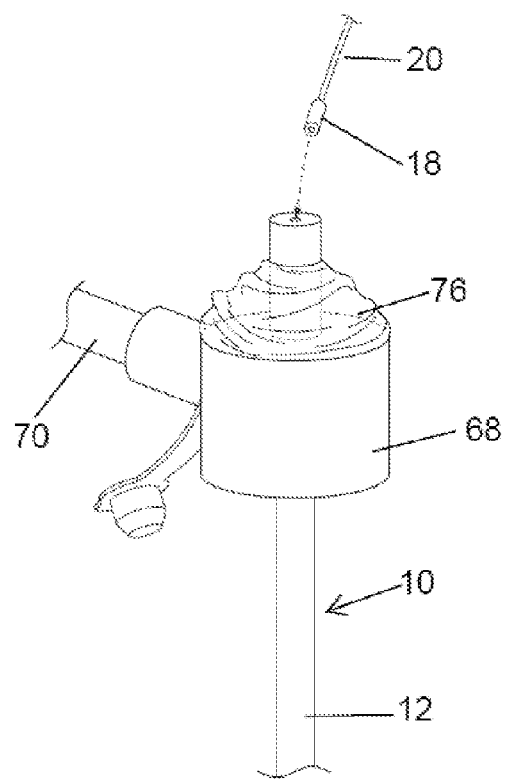
Figure 5C:
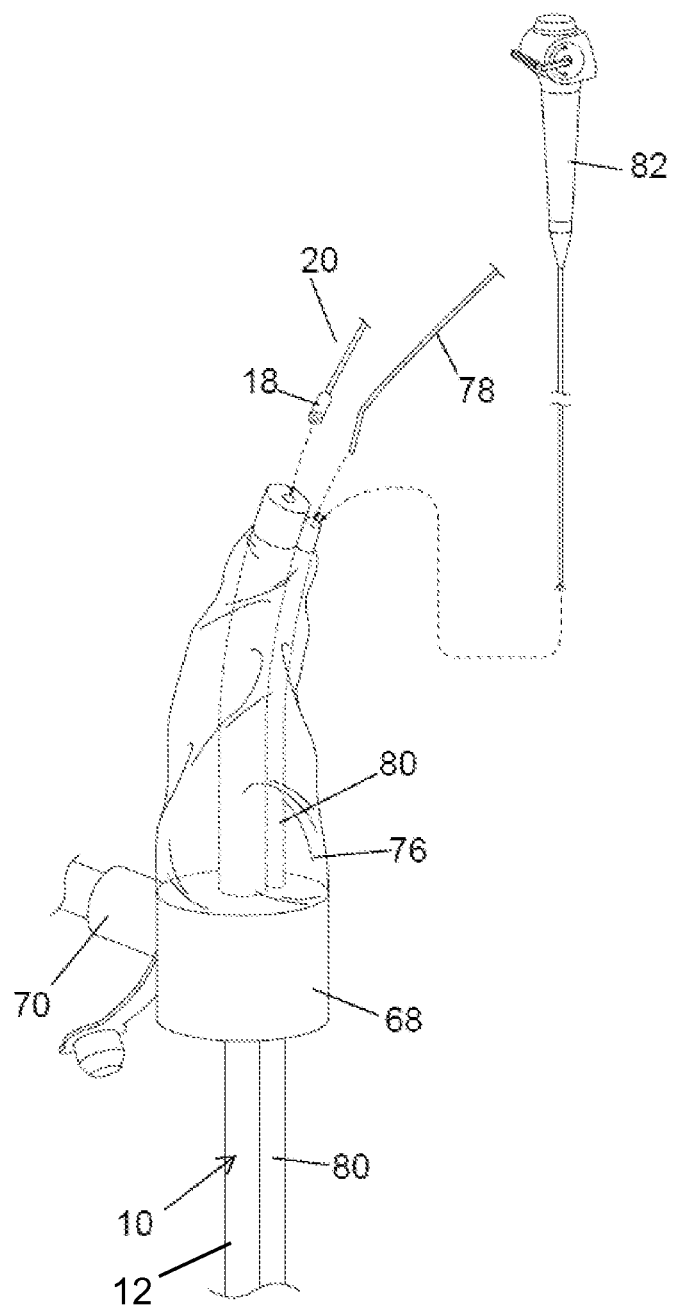

Further embodiments for a built-in ventilator adaptable cap 68 equipped with a visualization device 10 are shown in FIGS. 5A, 5B and 5C. As can be appreciated from FIG. 5A, the visualization device 10 comprises the camera 18 inside of the camera tube 12. The visualization device 10 is inserted through the ventilator adaptable cap 68. As shown in the embodiment of FIG. 5A, a plastic clear sleeve 76 can be attached over the adaptable cap 68 such that the sleeve 76 can slide up and down as shown in FIGS. 5A and 5B in the proximal-distal direction, which allows the visualization device 10 to remain sterile during insertion and removal. As the visualization device 10 is inserted and removed through the sleeve 76, the visualization device 10 remains sterile and free of contamination. The sleeve 76 is long enough to maintain the whole visualization device 10 outside the ventilation cap and remain sterile. A further embodiment is shown in FIG. 5C in which the visualization device 10 is inserted through the sleeve 76 as shown in FIGS. 5A and 5B, except a bougie 78 is added through a bougie tube 80.

The bougie 78 can be replaced with a flexible guided stylet 82 as shown in the insert to FIG. 5C which rotates and guides a stylet inside of a patient, which is protected from patient's tissues. If the tube 80 is used with a stylet, then the tube 80 has to be sealed at the distal end. Additional tubes can be attached and placed through the sleeve 76. Such tubes include, but are not limited to a suctions tube and a tool tube which can be used for delivering biopsy forceps and other tools. The assembly of the built-in ventilator adaptable cap 68 and visualization device 10 with the sleeve 76 can be used with any medical device to which a built-in ventilator adaptable cap can be attached, including an endotracheal tube as described in connection with FIG. 3, a supraglottic device or with a laryngeal mask airway. If an embodiment with a bougie or stylet is used as described in connection with FIG. 5C, the bougie 78 can protrude distally or slide independently from a medical device and guide the medical device movement inside of a patient during placement under visualization with the visualization device 10.

Figure 6A:
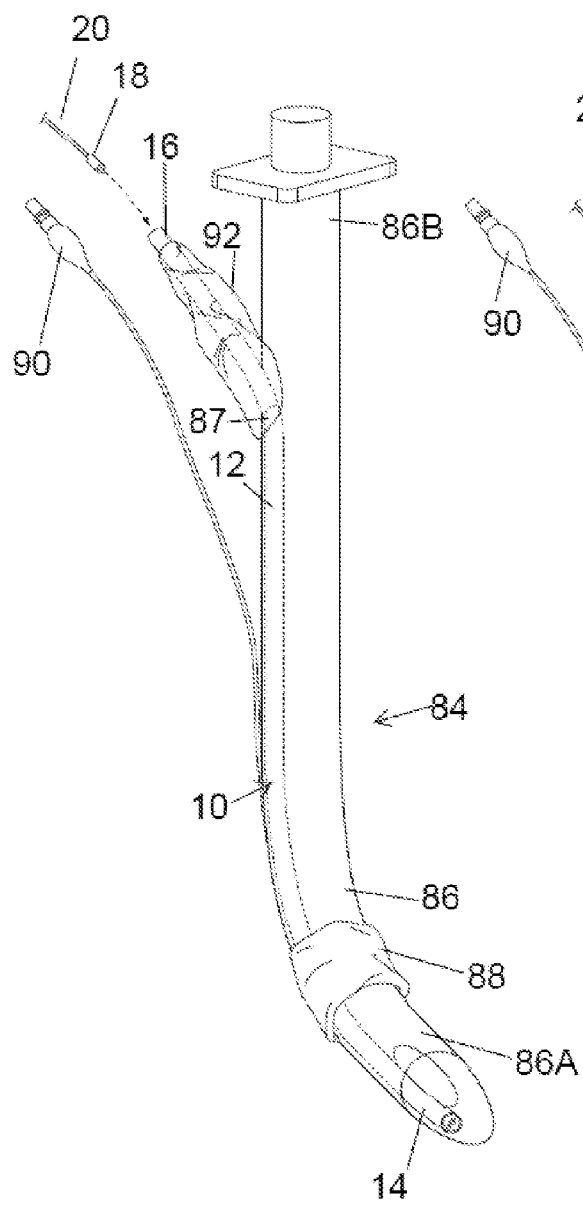
FIGS. 6A and 6B depict side views of an embodiment for an endotracheal device equipped with a visualization device delivered through a sliding sleeve.
Figure 6B:
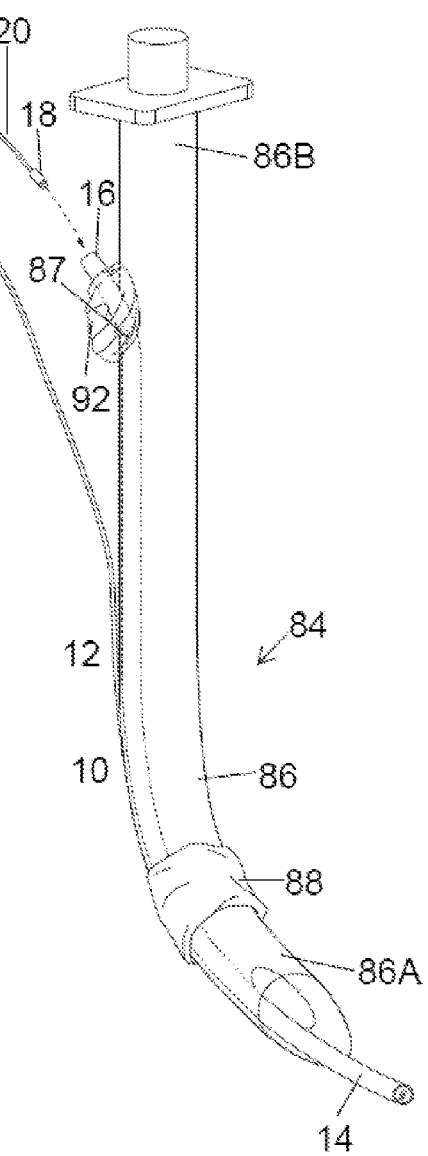

Further embodiments for an endotracheal device equipped with a visualization device, generally 84, are shown in FIGS. 6A and 6B. As can be appreciated from FIG. 6A, the visualization device 10 which comprises the camera 18 inside of the camera tube 12 can be inserted inside of an endotracheal tube 86 through an opening 87 on one side of the endotracheal tube 86. As shown in the embodiment of FIG. 6A, a plastic sleeve 92 can be attached over the opening 87 such that the sleeve 92 can slide up and down as shown in FIGS. 6A and 6B, which facilitates keeping the visualization device 10 sterile while it is moved in or out of the endotracheal tube 86. As the visualization device 10 is inserted and removed from the endotracheal tube 86 through the sleeve 92, the visualization device 10 remains sterile and free of contamination. The visualization device 10 can be removed entirely from the endotracheal tube 86 through the sleeve 92 and remain sterile. The endotracheal tube 86 may be equipped with a cuff 88 positioned near the distal end 86A. The visualization device 10 can move inside the endotracheal tube 86 along the proximal-distal (86B-86A) axis such that the visualization device 10 is distal to the cuff 88 or the visualization device 10 can protrude outside the endotracheal tube 86 distally as shown in FIG. 6B. This permits for obtaining images from a patient with the visualization device 10 after the cuff 88 is inflated with a device 90 and obtaining the images from the area in a patient's body which is distal to the cuff 88. This distal to the cuff 88 area is available for monitoring after the cuff 88 is inflated because of the visualization device 10 in which the camera 18 collects images through the transparent material 17 at the distal end 14.

In this embodiment, the visualization device can slide up and down inside of an endotracheal tube, which permits advancement and retraction of the camera tube 12 while maintaining sterility of an endotracheal tube into which the visualization device 10 can be inserted as described above. The camera 18 can be easily advanced inside of the camera tube 12 and provide inspection of the endotracheal tube through its length as well as distal to the tip of the endotracheal tube.

Figure 7A:
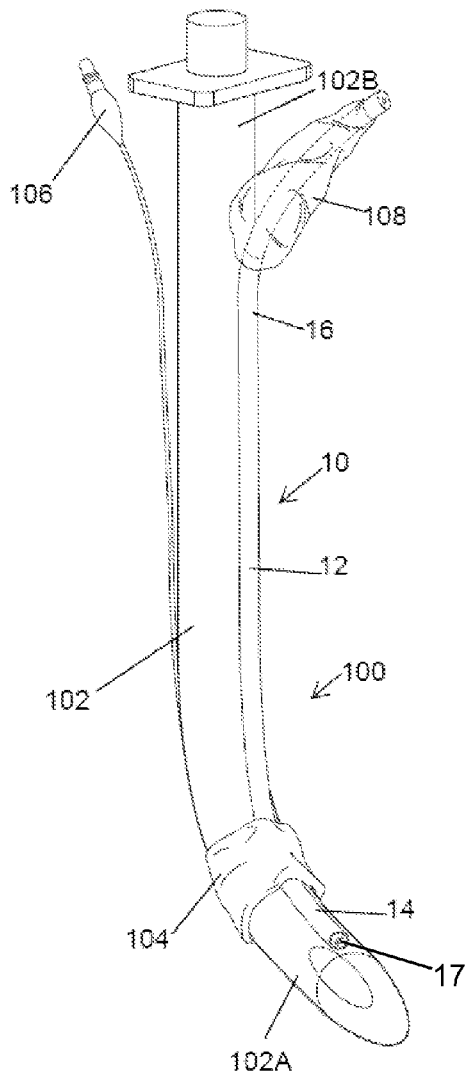
FIGS. 7A and 7B depict side views of an alternative embodiment for an endotracheal device equipped with a visualization device and delivered through a sliding sleeve.
Figure 7B:
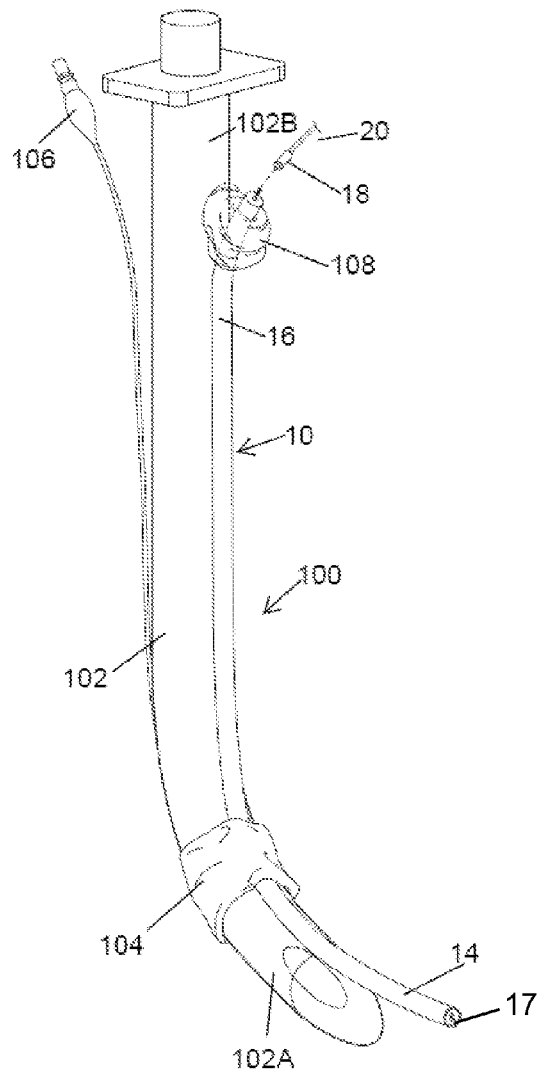

Further embodiments for an endotracheal device, generally 100, equipped with a visualization device 10 are shown in FIGS. 7A and 7B. Additional tubes can be attached to the tube 10 or be placed adjacent to the tube 10. Such tubes include, but are not limited to a suction tube, a tube for delivering instruments such as forceps, a bougie or flexible stylet. As can be appreciated from FIG. 7A, the visualization device 10 comprises the camera 18 inside of the camera tube 12 positioned externally on the endotracheal tube 102 and along the proximal-distal (102B-102A) axis. As shown in the embodiment of FIG. 7A, a plastic sleeve 108 can be attached to the endotracheal tube 102 such that the sleeve 108 can slide up and down outside the endotracheal tube 102 as shown in FIGS. 7A and 7B, which facilitates the movement of the visualization device 10 along the proximal-distal (102B-102A) axis of the endotracheal tube 102. As the visualization device 10 is inserted and removed through the sleeve 108, the visualization device 10 remains sterile and free of contamination. The endotracheal tube 102 may be equipped with a cuff 104 wrapped around the endotracheal tube 102 near its distal end 102A. The visualization device 10 moves outside the endotracheal tube 102 along the proximal-distal axis 102B-102A such that the visualization device 10 can be proximal to the cuff 104. This also permits for obtaining images from a patient with the visualization device 10 after the cuff 88 is inflated with a device 106 The camera tube 12 can slide proximal or distal of the cuff 104. Thus, at least in some embodiments, the camera tube 12 would be into a sealed tunnel.

Figure 8:
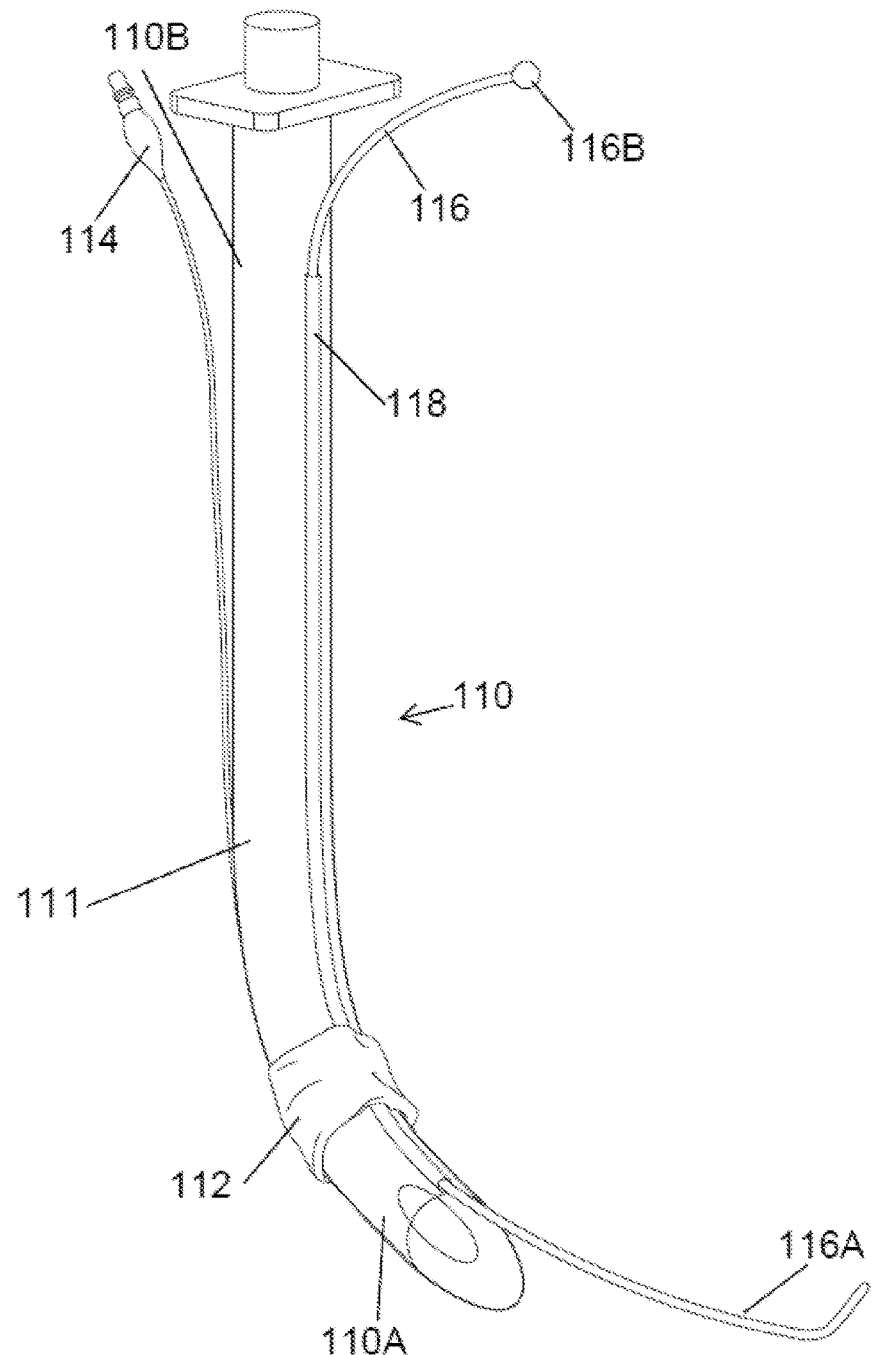
FIG. 8 is a side view of an embodiment for an endotracheal device equipped with a bougie.

FIG. 8 depicts a further embodiment of an endotracheal device, generally 110. The device 110 can be equipped with the visualization device 10 and the sound tube 40 described in connection with FIG. 2 (not shown). The endotracheal device is further equipped with a bougie 116 which can slide up and down along the proximal-distal (116B-116A) axis inside of a tube 118 which is attached externally to the endotracheal tube 111. The endotracheal tube 111 is equipped with a cuff 112 located in proximity to a distal end 110A of the tube. The cuff 112 can be inflated with a device 114 after the endotracheal device 110 is placed inside of a patient. The visualization device 10 can be sealed or attached to the endotracheal tube 111 either outside or inside as described above in connection with embodiments provided by FIGS. 2, 3, 4A, 4B, 5A, 5B, 6A, 6B, 7A and 7B. The bougie 116 guides the movement of the endotracheal device 111 during placement in a patient under visualization with the visualization device 10 and permits guided sliding down the medical device over the bougie 116 inside of the patient's airway.

Figure 9:
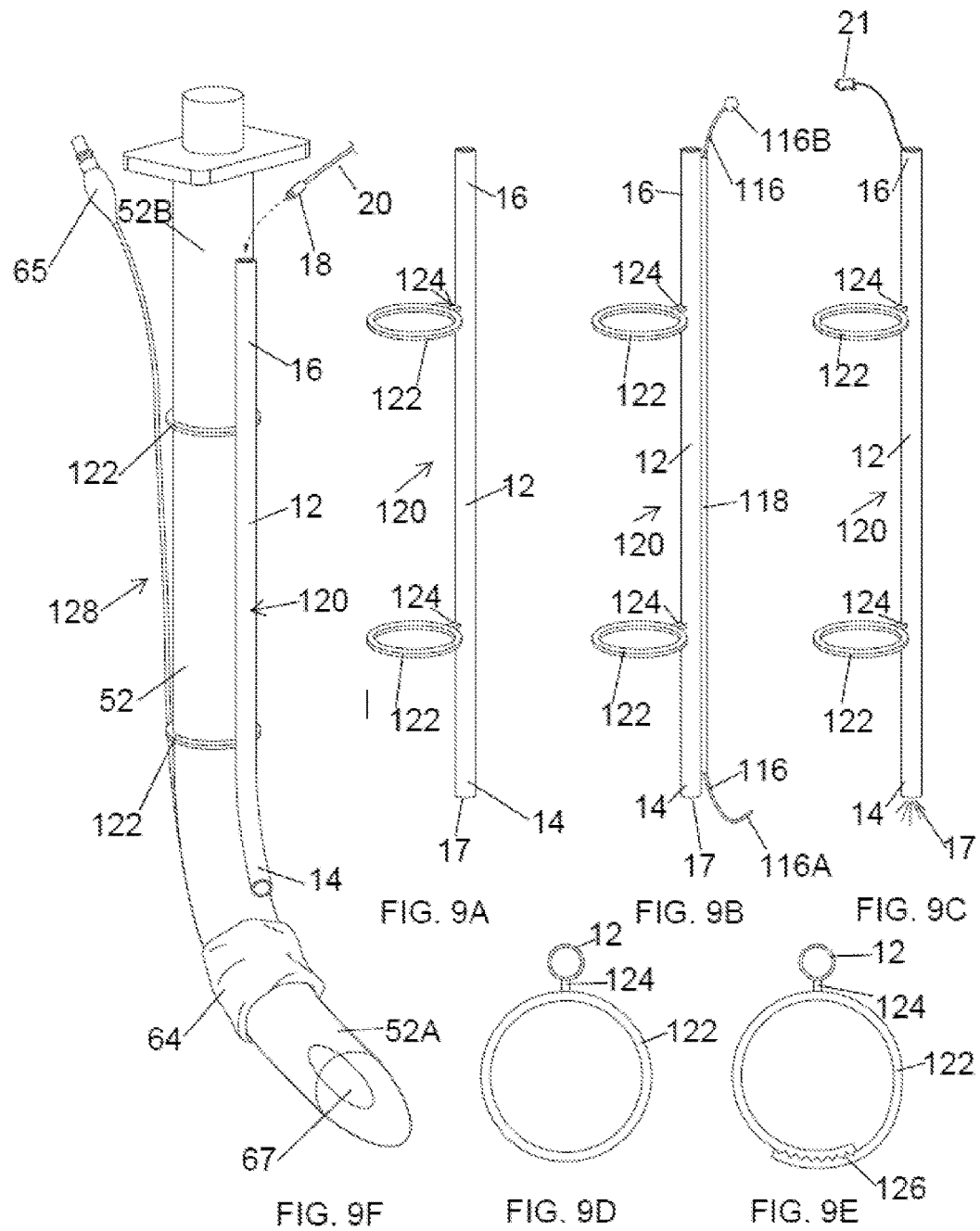
FIGS. 9A, 9B and 9C are a side view of a visualization device equipped with rings.
FIG. 9D is a cross-sectional view through the visualization device of FIG. 9A showing a ring connected to the camera tube.
FIG. 9E is a cross-sectional view through the visualization device of FIG. 9A showing an adjustable sliding ring with a clasp connected to the camera tube.
FIG. 9F is a side view of an endotracheal tube to which the visualization device of FIG. 9A is connected with two sliding rings.

Further embodiments of a visualization device, generally 120, are shown in FIGS. 9A-9C. As shown in FIG. 9A, the camera tube 12 can be equipped with at least one, and preferably two external rings 122 which are sealed or otherwise connected by means 124 to the camera tube 12. In some embodiments, one ring 122 is positioned at about ⅓ of the camera tube length from the proximal end 16 and the other ring is positioned at about ⅔ of the camera tube length from the proximal end. While in the embodiment of FIG. 9A, the camera tube 12 is equipped with two rings 122, other embodiments include those in which more than 2 rings are used or only one ring is used. The positioning of the rings along the proximal-distal (16-14) axis of the camera tube 12 can also vary. Other modalities include a clasp or a plastic band to hold the camera tube 12.

As in all other embodiments, the camera tube 12 has a distal end 14 sealed with a transparent material 17 and a proximal end 16 with an opening through which a camera 18 is inserted into the camera tube 12. As shown in FIG. 9B, the visualization device 120 can be further equipped with a tube 118 sealed or otherwise attached externally along the proximal-distal (16-14) axis of the camera tube 12. A bougie 116 is placed inside of the tube 118 such that a distal end 116A of the bougie 116 protrudes distally over the camera tube 12, while its proximal end 116B extends outside the visualization device 120 proximally and can be used by a medical provider to rotate the distal end 116A and in this way guide the movement of the visualization device 120 along with a medical device to which it is attached.

As shown in FIG. 9C, the visualization device 120 can be further equipped with a light source 21 which can be either built in the camera tube 12, built in the camera 18 or it can be kept outside the visualization device 120 and outside the patient's body. The visualization device 120 is attached to a medical device with the rings 122, and this permits for customized positioning of the visualization device 120 as it can slide up and down along a proximal-distal axis of a medical device.

As shown in a cross-sectional view in FIG. 9D, the ring 122 can be of any diameter in order to fit on a medical device of choice. As shown further in FIG. 9E, at least in some embodiments the ring 122 may have a clasp 126 such that the diameter of the ring 122 can be adjusted according to a diameter of a medical device to which the visualization device 120 is attached with the rings 122.

An embodiment as shown in FIG. 9F provides an assembly, generally 128, in which the visualization device 120 is attached with the rings 122 to an endotracheal tube 52. The rings 122 can slide up and down along the proximal-distal (52B-52A) axis of the endotracheal tube 52, and in this way the position of the visualization device 120 can be adjusted with respect to the endotracheal tube 52. Further, the rings 122 can rotate around the endotracheal tube 52, which permits altering the positioning of the camera device 120 if images are needed from a different area inside of a patient.

Because the rings 122 can be adjustable, the visualization device 120 can be used with an endotracheal tube of any size, including those for pediatric patients. Further, the visualization device 120 with at least two rings connected externally to the camera tube 12 can be provided as a kit, and a medical practitioner can assemble the visualization device with any conventional endotracheal tube or any other conventional medical device for which visualization and monitoring are needed at the time of treatment.

Further embodiments provide an intubation method in which an endotracheal tube, including any of the endotracheal tubes described above and equipped with the visualization device as described above, is placed in patient's airway and positioned under the patient's vocal cords under constant visualization by the visualization device 10.

Figure 10:
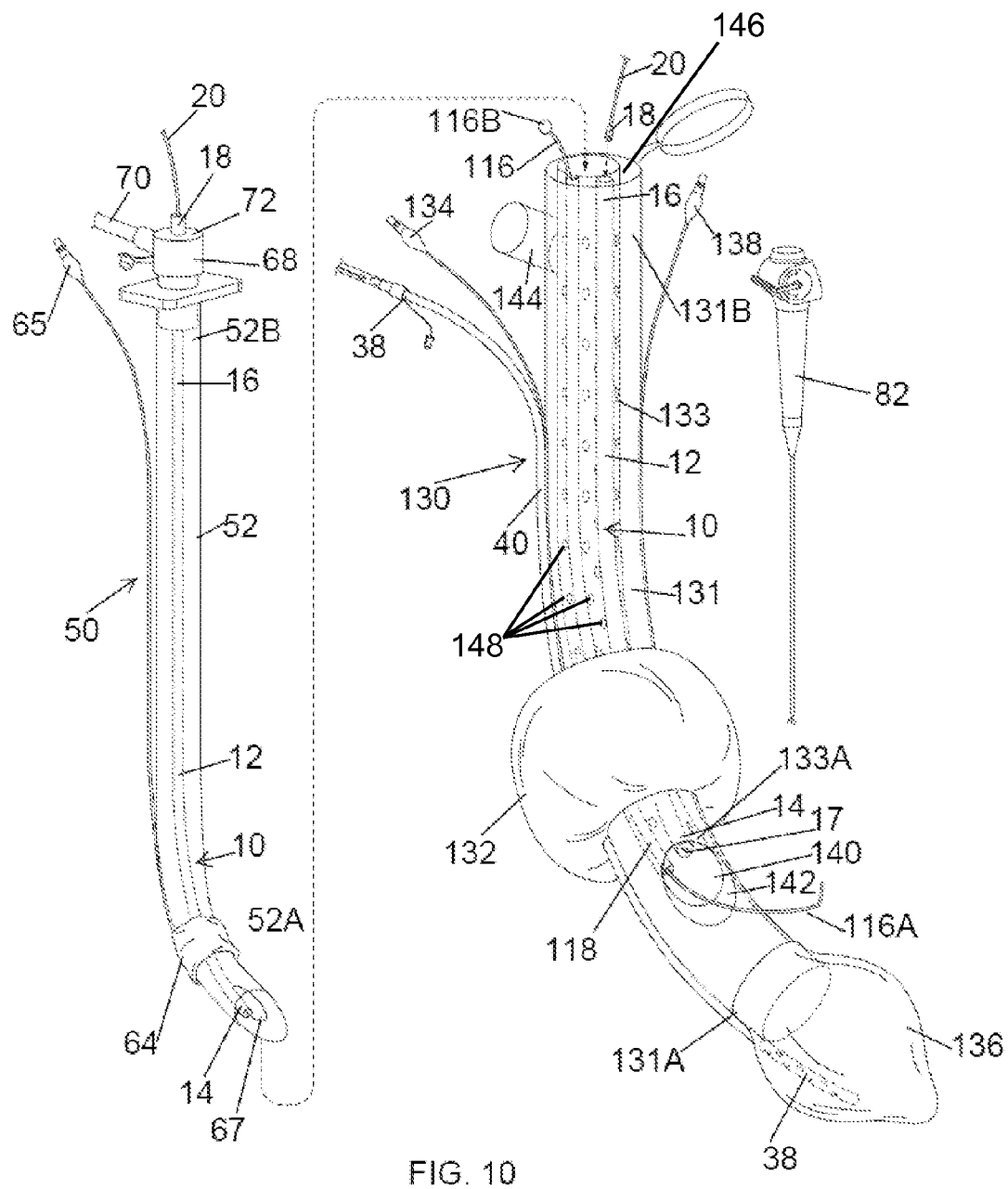
FIG. 10 is a side view of a supraglottic airway device equipped with a visualization device. An endotracheal device of FIG. 3 is shown as an insert on the left and a flexible guided stylet is shown as an insert on the right.

Referring to FIG. 10, it depicts a side view of a supraglottic airway device, generally 130. Any standard endotracheal tube known in the art and an endotracheal device of FIG. 3 is shown in the insert on the left of FIG. 10 can be used in combination with the supraglottic airway device 130.

The supraglottic airway device 130 comprises a supraglottic tubal body 131 with a distal end 131A and a proximal end 131B and a lumen 146. The supraglottic airway device 130 includes a designated intubation tube 133 which is inserted into the lumen 146 and into which an endotracheal device 50 can be placed as shown in FIG. 10. The distal end 133A of the intubation tube 133 ends with an elliptical opening 140 which is located distally from a cuff 132 which can be inflated with a device 134. The intubation tube 133 has a plurality of holes 148 distributed throughout its body to allow ventilation from outlet 144 through tubal body 131.

While a standard endotracheal device, including an endotracheal device 50, may be equipped with a visualization device, the supraglottic airway device 130 comprises its own visualization device 10 which is placed in the lumen 146. The visualization device 10 comprises a camera tube 12 with a distal end 14 and a proximal end 16. The distal end 14 is sealed with a transparent material 17. The camera tube 12 is sealed or otherwise attached externally to the intubation tube 133 along the proximal-distal (131B-131A) axis. The supraglottic device 130 can be further equipped with a bougie 116 which is located inside of the tube 118. The tube 118 is placed inside of the lumen 146 and such that the distal end 116A of the bougie 116 protrudes from the tube 118 and outside the suproglottic tubal body 131 through an elliptical opening 142 which is located on the supraglotic tubal body 131 slightly proximally from the distal end 131A. The elliptic opening 142 of the supraglottic tubal body 131 overlaps partially with the elliptic opening 140 of the intubation tube 133. The bougie tube has its own opening through 140.

At the distal end 131A, the tubal body 131 is capped with a balloon 136 which can be inflated with a device 138. In some embodiments, the bougie 116 can be replaced with a flexible guided stylet 82 shown on the right of FIG. 10.

In addition to the visualization device 10, the supraglottic device 130 can be also equipped with a sound- and temperature-monitoring device 38 which is located inside a tube 40 which is sealed or otherwise attached externally to the tubal body 131 along the proximal-distal (131B-131A) axis. The sound device 38 can monitor patient's heart beat and breathing after the supraglottic device 130 is placed inside of the patient. On its proximal end 131B, the tubal body 131 may be connected to a ventilator (not shown) though an outlet 144. Because the supraglottic device 130 can ventilate in a closed circuit through the tubal body 131, an endotracheal tube 50 can be placed inside of the intubation tube 133 without the need to stop ventilation and therefore, the supraglottic device 130 provides continuous ventilation, continuous visualization in real time through the visualization device 10 and continuous sound and temperature monitoring by the sound monitoring device 38 with a temperature probe. This real time information can be transferred or stored to multiple distant monitoring sites.

Other advantages for the supraglottic airway device include the ability to intubate, extubate and to easily reintubate if needed under continuous ventilation and the ability to continuously visualize vocal cords and supraglottic structures. The device 130 is suitable for applications in children and adults. Further, the device 130 is equipped with the cuff 132 for blocking the pharynx and the balloon 136 which blocks the esophagus after the device 130 is placed in a patient. Furthermore, an endotracheal tube can be placed just proximal to the vocal cords in the tubal body 133. This permits ventilation through 144 and tubal body 131 uninterrupted.

Figure 11A:
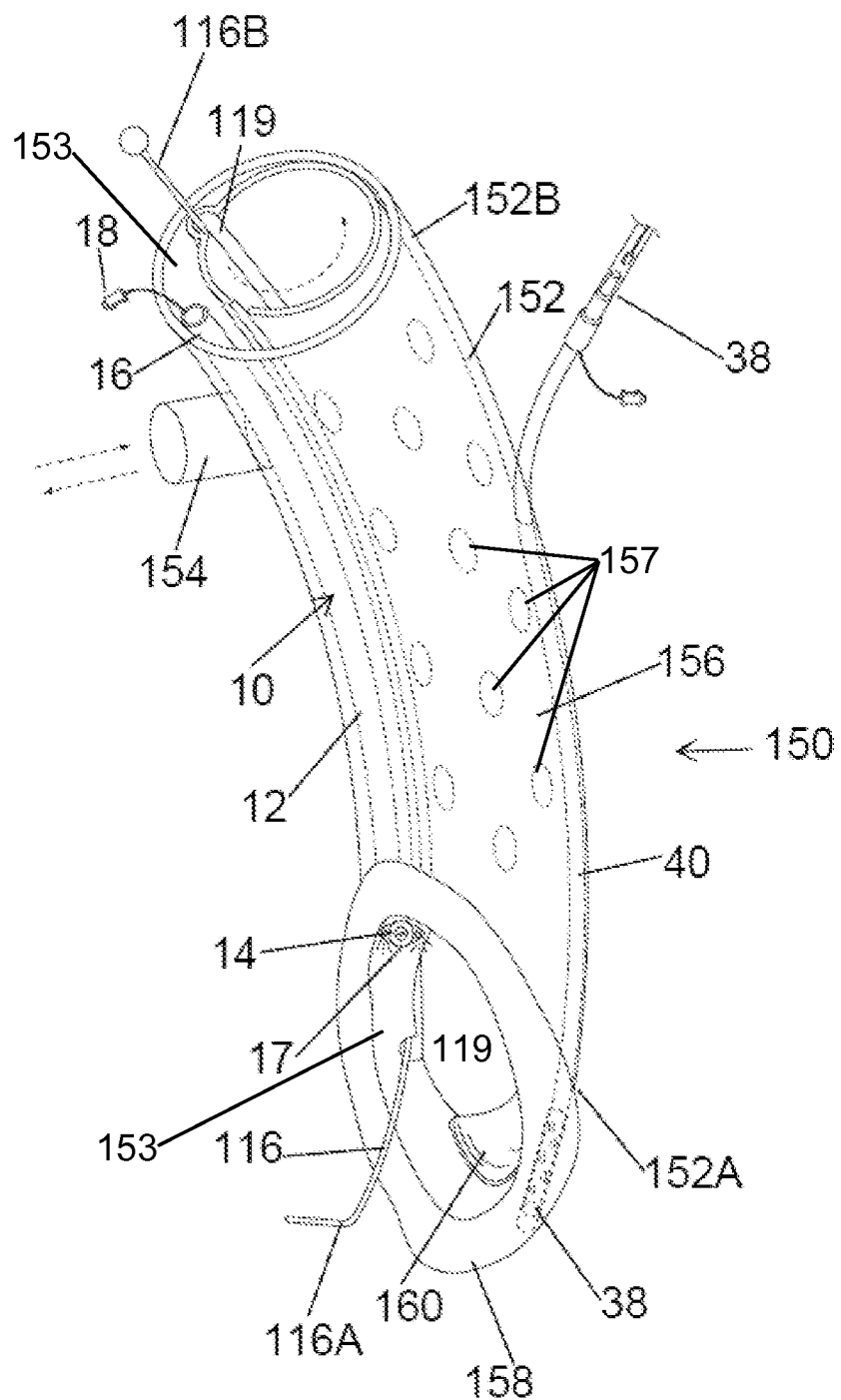
FIGS. 11A and 11B depict a side view of an alternative airway device with a visualization device.
Figure 11B:
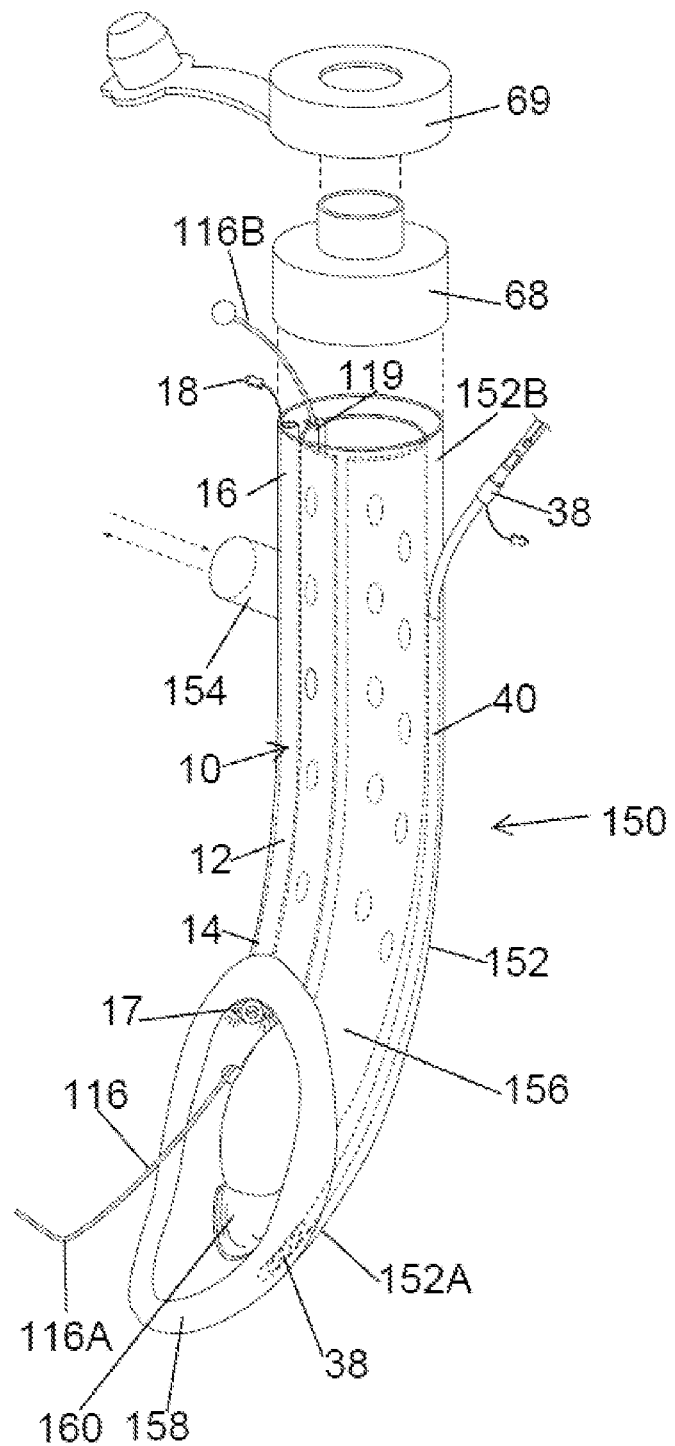

Referring to FIGS. 11A and 11B, an alternative embodiment for an airway device, generally 150, is provided. This device can be used in pediatric and adult patients as it is adoptable to different sizes. It provides continuous visualization of supraglottic structures and it can be advanced, retracted, or rotated, side to side to provide direct visualization of vocal cords. As can be appreciated from FIGS. 11A and 11B, the airway device 150 comprises a tubal body 152 with a distal end 152A and a proximal end 152B and a lumen 153. The tubal body 152 may be connected to a ventilator through an outlet 154. A visualization device 10 is sealed or otherwise attached inside of the tubal body 152 along the proximal-distal (152B-152A) axis on at least one side. The visualization device 10 comprises a camera tube 12 with a distal end 14 and a proximal end 16. The camera tube 12 is sealed at the distal end 14 with a transparent material 17. The proximal end 16 of the camera tube 12 remains open and a camera 18 is inserted in the camera tube 12 through the proximal end 16. The camera 18 does not come in contact with a patient's body and it does not have to be sterilized, it does not have to be disposable, although it may be disposable in at least some applications. The visualization device 10 can be further equipped with a light source which can be built in the camera tube 12 or be a part of the camera 18. In alternative, a light source may be left outside the camera tube 12, but still shed enough light inside of the camera tube 12 for the camera 18 to obtain images inside of a patient's body.

An intubation tube 156 is placed inside of the lumen 153 of the tubal body 152 along the proximal-distal (152B-152A) axis. The intubation tube 156 shares a lumen 119 with a bougie 116 which is inserted inside the lumen 119 along the proximal-distal (152B-152A) axis such that a distal end 116A of the bougie 116 may protrude outside the tubal body 152 at the distal end 152A and proximal end 116B may protrude outside the tubal body 152 and the proximal end 152B can be used by a medical practitioner to guide the movement of the airway device 150 with the bougie 116 during placement in a patient, including advancing the bougie 116 through patient's vocal cords under direct visualization by camera 18. The intubation tube 156 has a plurality of holes 157 distributed along the intubation tube 156.

At least in some embodiments, the airway device 150 is further equipped with a sound- and temperature-monitoring device 38 which can be inserted in a tube 40 which is sealed or otherwise attached inside of the tubal body1 52 along the proximal-distal (152B-152A) axis such as the distal end of the sound-monitoring device 38 is positioned at or near the distal end 152A of the tubal body 152, which is also equipped with a cuff 158 along the perimeter of the tubal body 152 at the distal end 152A. The intubation tube 156 is designed such that at least in some embodiments the intubation tube 156 has a ramp 160 at the distal end 152A of the airway device 150. A standard endotracheal tube, including those described in various embodiments above, can be placed inside of the lumen 119 in the intubation tube 156 for positioning in a patient.

As shown in FIG. 11B, a ventilator adaptable cap 68 and a lid 69 are attached to the tubal body 152 at the proximal end 152B. The endotracheal tube is inserted into the device 150 through the cap 68. Using the cap 68 with the lid 69 on the airway device 150 is preferred when ventilation is accomplished through an outlet 154.

Figures 12A, 12B, 12C:
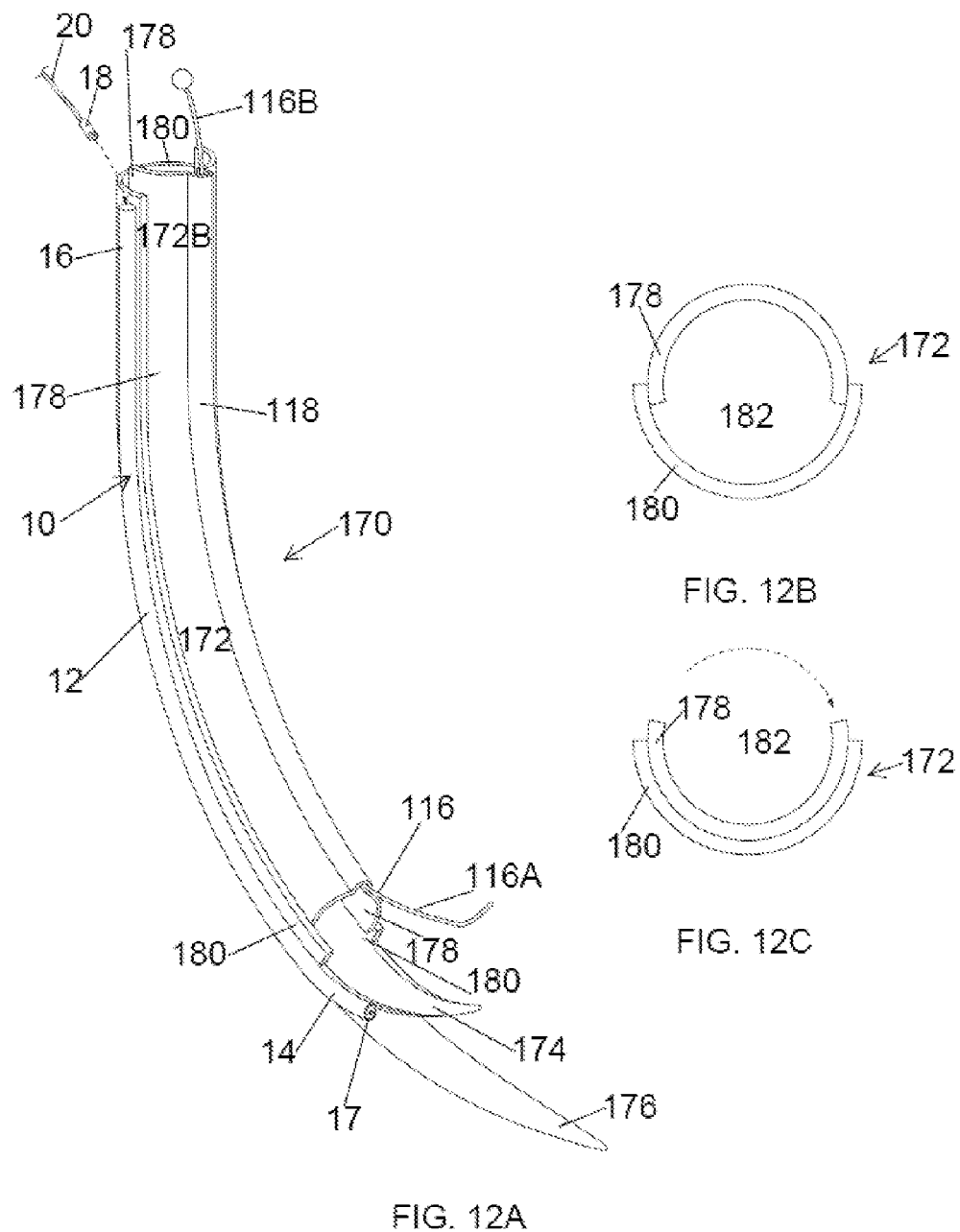
FIGS. 12A, 12B and 12C depict an oral airway intubating device with a visualization device.

Yet another embodiment for an oral airway device, generally 170, is provided as shown in FIGS. 12A, 12B and 12C. As can be appreciated from FIG. 12A, the airway device 170 comprises a tubal body 172 with a distal end 172A and a proximal end 172B. The tubal body 172 ends with two ramps 174 and 176 at the distal end 172B. As can be appreciated from a side view in FIG. 12A and cross-sectional views of the tubal body 172 in FIGS. 12B and 12C, the tubal body 172 is made of two half-cylinders 178 and 180. The half-cylinder 178 is slightly smaller in diameter than the half-cylinder 180. The tubal body 172 can be present in one of the two forms: as a full cylinder shown in FIG. 12B or as a half-cylinder as shown in FIG. 12C. The half-cylinder 178 and the half-cylinder 180 are connected by means such that the half-cylinder 178 can rotate and retract into the half-cylinder 180. The half-cylinder form of FIG. 12C is achieved by the half-cylinder 178 rotating at about 180 degrees and aligning with the half-cylinder 180 such that the half-cylinder 178 is located inside of the half-cylinder 180 as shown in FIG. 12C.

A visualization device, generally 10, is sealed or otherwise attached externally to the half-cylinder 180 along the proximal-distal (172B-172A) axis. The visualization device 10 comprises of a camera tube 12 with a distal end 14 and a proximal end 16. The distal end 14 is sealed with a transparent material 17. A camera 18 is placed through an opening at the proximal end 16 into the camera tube 12 and is moved inside the camera tube 12 to the distal end 14.

Similarly to all other embodiments, the camera 18 does not come in contact with a patient's body, and it does not have to be disposable, does not have to be sterilized and it can be reused in multiple devices. The camera 18 is connected with wire 20 to at least one monitoring device and it transmits images in real time. The camera 18 can be connected wirelessly to at least one monitoring device which can be positioned at some remote location. A light source can be added as described in connection with the visualization device in other applications.

The half-cylinder 180 ends in two ramps 174 and 176 at the distal end 172A. The ramp 174 is smaller in size than the ramp 176 and the two ramps are superimposed over each other such as the smaller ramp 174 is proximal to a lumen 182 created by half-cylinders 178 and 180 when they are in the full-cylinder form as shown in FIG. 12B, while the ramp 176 is distal to the lumen 182. The ramps 174 and 176 are flexible and absorb the shock from sliding and releasing an endotracheal tube which can be delivered into a patient by the oral airway device 170. The ramps also facilitate the removal of the oral airway device 170 after the endotracheal tube is placed inside of the patient.

As shown in FIG. 12A, the oral airway intubating device 170 can be further equipped with a bougie 160 which can be inserted into a tube 118 along the proximal-distal (172B-172A) axis such that a distal end 116A of the bougie 116 protrudes distally from the oral airway device 170 and a proximal end 116B protrudes outside the oral airway device proximately and can be used to manipulate the distal end 116A of the bougie 116 such that it guides the movement of the airway device 170 during placement in a patient. The bougie tube 118 is located on the smaller half-cylinder 178 and it shares the lumen 182 with the tubal body 172.

Figures 13, 14A:
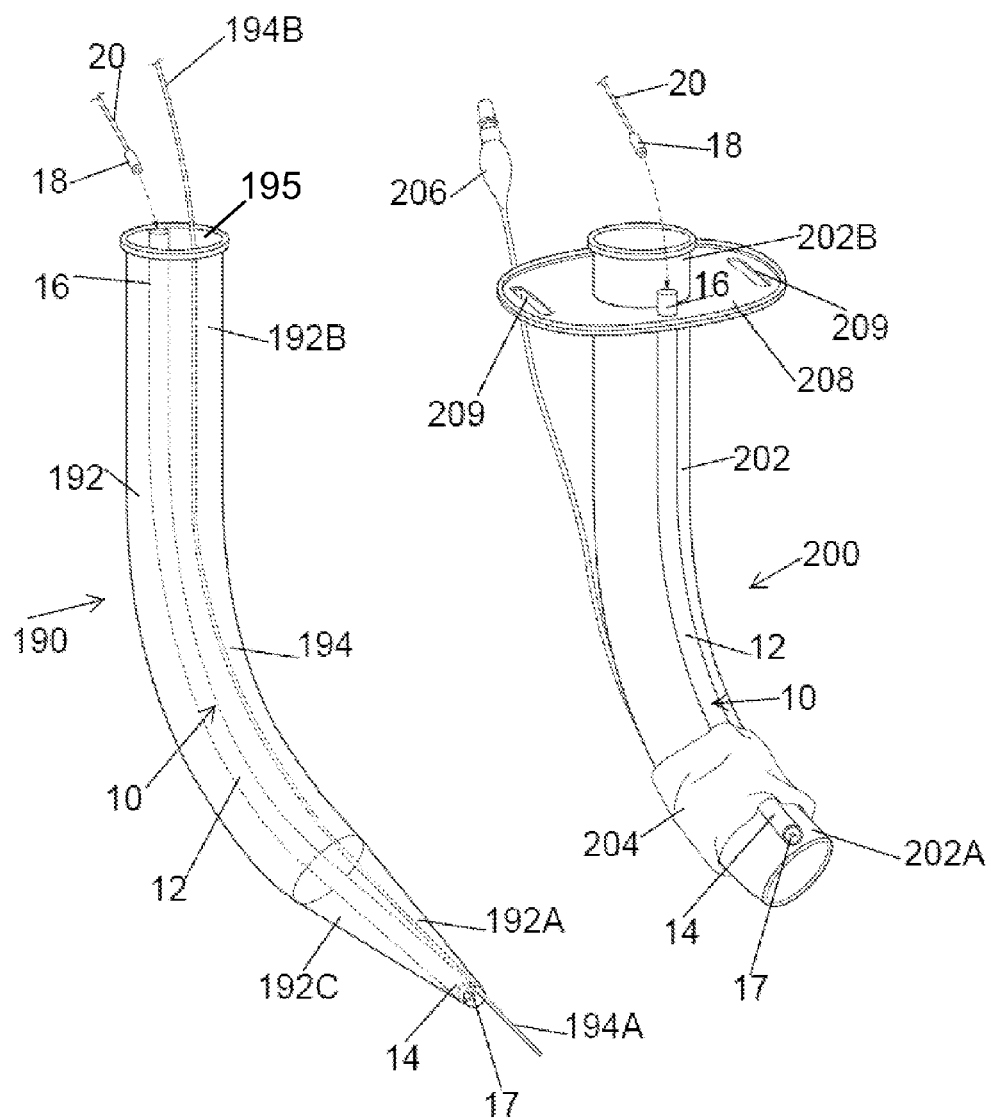
FIG. 13 depicts a side view of a dilator with a visualization device.
FIGS. 14A and 14B depict a side view of a tracheostomy device with a visualization device.

A further embodiment provides a dilator with a visualization device, generally 190 in FIG. 13. As can be appreciated from FIG. 13, the dilator 190 comprises a tubal body 192 with a proximal end 192B and a distal end 192A. A certain distal portion of the tubal body 192 is tapered into a conical shape 192C such that the opening at the distal end 192A of the tubal body 192 is significantly smaller in diameter in comparison to an opening at the proximal end 192B. A visualization device 10 is positioned inside of a lumen 195 of the tubal body 192 and along the proximal-distal (192B-192A) axis. The visualization device 10 may be sealed or otherwise attached inside of the tubal body 192. The visualization device 10 is essentially the same device as shown in FIG. 1A, and it comprises a camera tube 12 with a proximal end 16 and a distal end 14. The distal end 14 of the camera tube 12 is in close proximity with the distal end 192A of the tubal body 192. A camera 18 which can be either disposable or reusable is placed inside of the camera tube 12 through an opening at the proximal end 16 and all the way down to the distal end 14 of the camera tube 12, which is sealed with a transparent material 17. Just like other embodiments, the visualization device 10 can be equipped with a light source located outside of the dilator 194 or built in the camera tube 12. In some embodiments, the light source can be built in the camera 18.

As shown in FIG. 13, the camera 18 is connected by electrical wire 20 to a monitoring device (not shown). In some embodiments, the camera 18 can be in communication with a monitoring device wirelessly. A guide wire at the proximal end 194A is positioned inside of the lumen 195 of the tubal body 192. A proximate end 194B of the guide wire 194 protrudes outside of the tubal body 192 at the proximal end 192B The visualization device 10 verifies appropriate placement of the dilator device 190 and allows mobility of continuous visualization as dilation proceeds. The dilator device 190 is especially well suited for use with the Seldinger technique.

Further embodiments provide various tracheostomy tubes equipped with a visualization device. FIG. 14A depicts a side view of an embodiment for a tracheostomy device, generally 200. The device 200 comprises a tubal body 202 with a distal end 202A and a proximal end 202B. An inflatable cuff 204 is wrapped around the tubal body 200 in some proximity to the distal end 202A, but never at the very distal end 202A. The cuff 204 can be inflated with a device 206 after proper placement of the device 200 in a patient. At the proximal end 202B, the tubal body 202 protrudes through a plastic plate 208 such that some portion of the tubal body 202 is proximal to the plastic plate and will remain outside of a patient's neck after the device 202 is positioned in the patient. The plastic plate 208 may be oval in shape with the tubal body 202 protruding from the plate in the middle of the oval plastic plate 208. The plastic plate 208 may have two openings 209, one on each side of the plate such that the device 200 can be secured around patient's neck with some bandage by tying the device 200 through the openings 209 around patient's neck.

In the embodiment of FIG. 14A, the visualization device 10 is sealed or otherwise attached to the tubal body 202 externally. The visualization device 10 comprises a camera tube 12 which is sealed or otherwise attached externally along the proximal-distal (202B-202A) axis to the tubal body 202. The camera tube 12 is placed under the cuff 204 such that the cuff 204 wraps over the camera tube 12 and a distal end 14 of the camera tube 12 is distal to the cuff 204. The distal end 14 is sealed with a transparent material 17. A proximal end 16 of the camera tube 12 protrudes through the plastic plate 208 and remains outside of patient's neck. A camera 18 can be placed inside of the camera tube 12 through an opening in the proximal end 16. The camera 18 is not disposable, does not need to be sterilized and can be easily removed from the camera tube 12. The camera 18 is connected by electrical wire 20 to a monitoring device. In further embodiments, the camera 18 can be in communication with a monitoring device wirelessly. A light source can be added to the visualization device 10 as was described in other embodiments above.

Figure 14B:
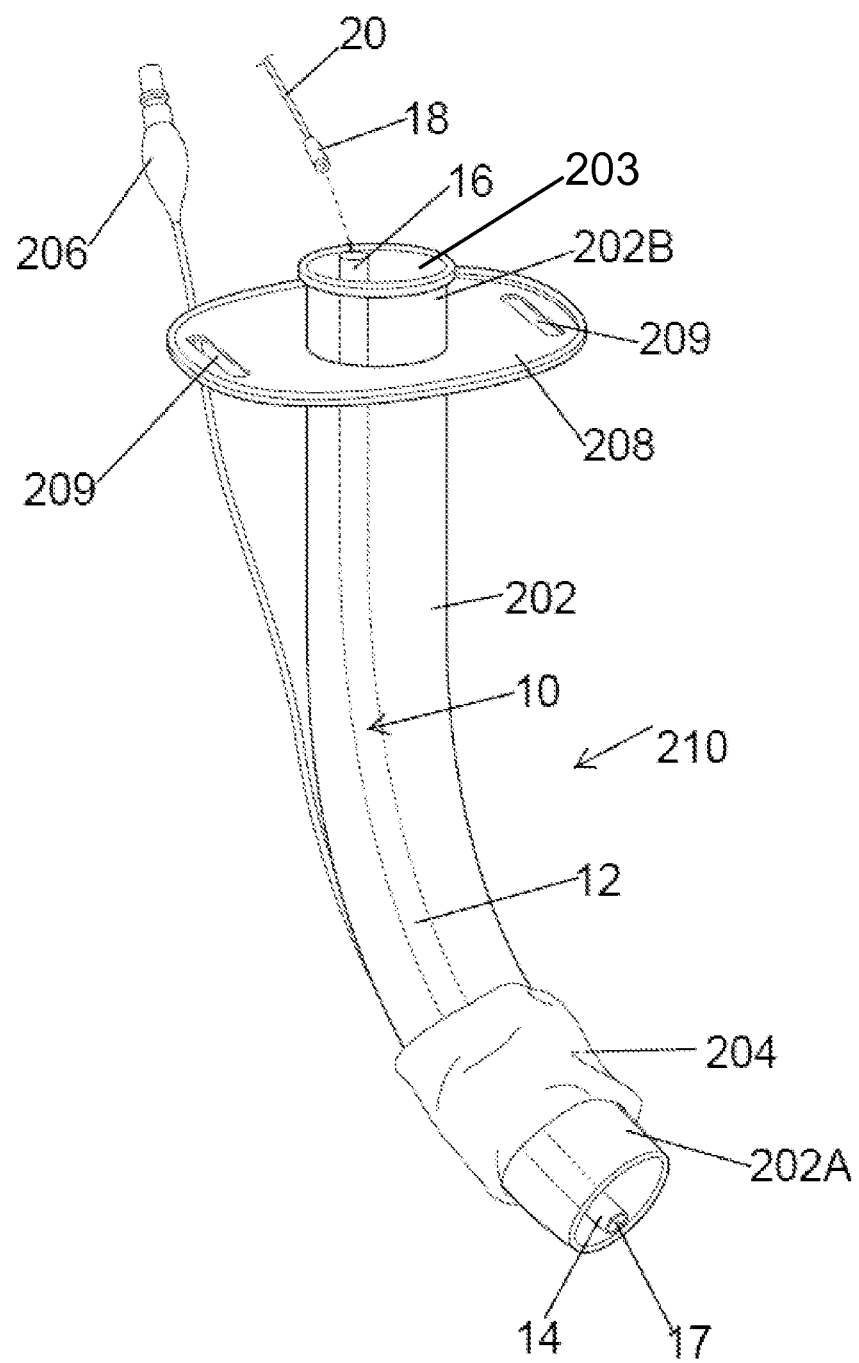

FIG. 14B depicts another embodiment for a tracheosomy device, generally 210. In this embodiment, the device 210 comprises of the same tubal body 202, cuff 204, plate 208 and other components as was discussed in connection with the device 200. However, unlike the device 200, a visualization device 10 is placed inside of a lumen 203 of the tubal body 202. The visualization device 10 comprises a camera tube 12 with a distal end 14 and a proximal end 16. The camera tube 12 may be sealed or otherwise attached internally to the tubal body 202 along the proximal-distal (202B-202A) axis such as the distal end 14 of the camera tube 12 is in close proximity with the distal end 202A of the tubal body 202. The distal end 14 is sealed with a transparent material 17. A camera 18 is placed inside of the camera tube 12 through an opening at the proximal end 16 which remains outside of the patient's neck after the device 210 is placed in the patient. The camera 18 is connected by electrical wire 20 to a monitoring device. In other embodiments, the camera 18 communicates with a monitoring device wirelessly. In some embodiments, the visualization device 10 comprises a light source.

Figure 15:
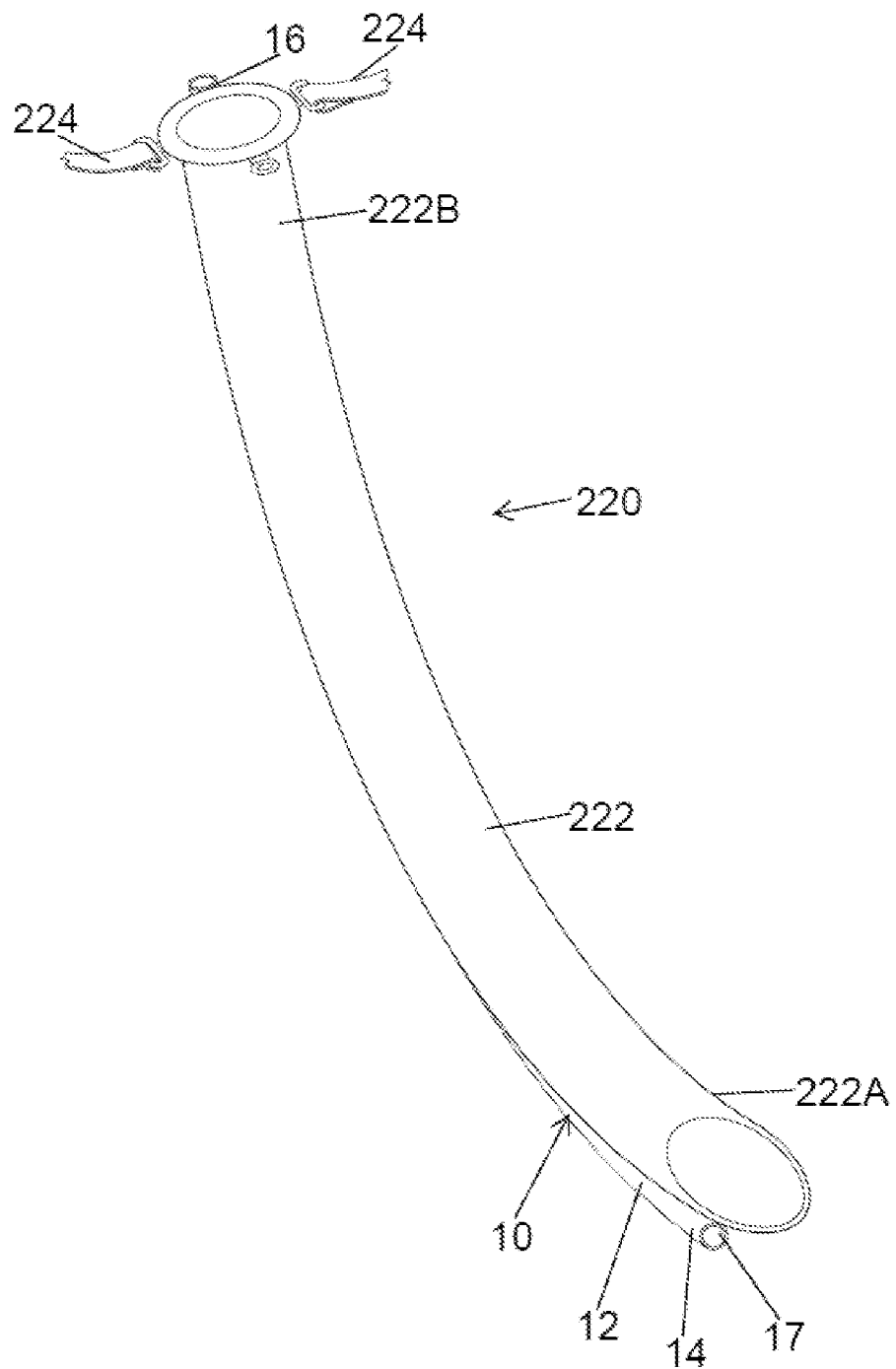
FIG. 15 depicts a side view of a nasal trumpet with a visualization device.

A further embodiment provides a nasal trumpet with a visualization device, generally 220 in FIG. 15. The trumpet 220 comprises a tubal body 222 with a proximal end 222B and a distal end 222A. Two fasteners 224 are attached at the proximal end 222B of the tubal body 222. After placing the trumpet 220 in a patient, the proximal portion of the tubal body 222 with the fasteners 224 remains outside of the patient, and the fasteners 224 can be used to secure the trumpet 220 around the patient's head.

A visualization device 10 is sealed or otherwise attached to the tubal body 222 externally along the proximal-distal (222B-222A) axis. The visualization device 10 comprises a camera tube 12 with a proximal end 16 and a distal end 14. The distal end is in near proximity with the distal end 222A of the tubal body 222. The distal end 14 is sealed with a transparent material 17. A camera 18 is placed inside of the camera tube 12 through an opening at the proximal end 16. The camera 18 is moved all the way to the distal end 14 and collects images in real time inside of a patient's body during placement of the device 220 as well as after the device 220 has been properly placed and secured. As in other embodiments, the camera 18 does not come in contact with patient's body, does not have to be sterilized and can be reused in multiple devices or in different patients. The camera 18 communicates with a monitoring device (not shown) either with electrical wire 20 or wirelessly, or both.

Figure 16D:
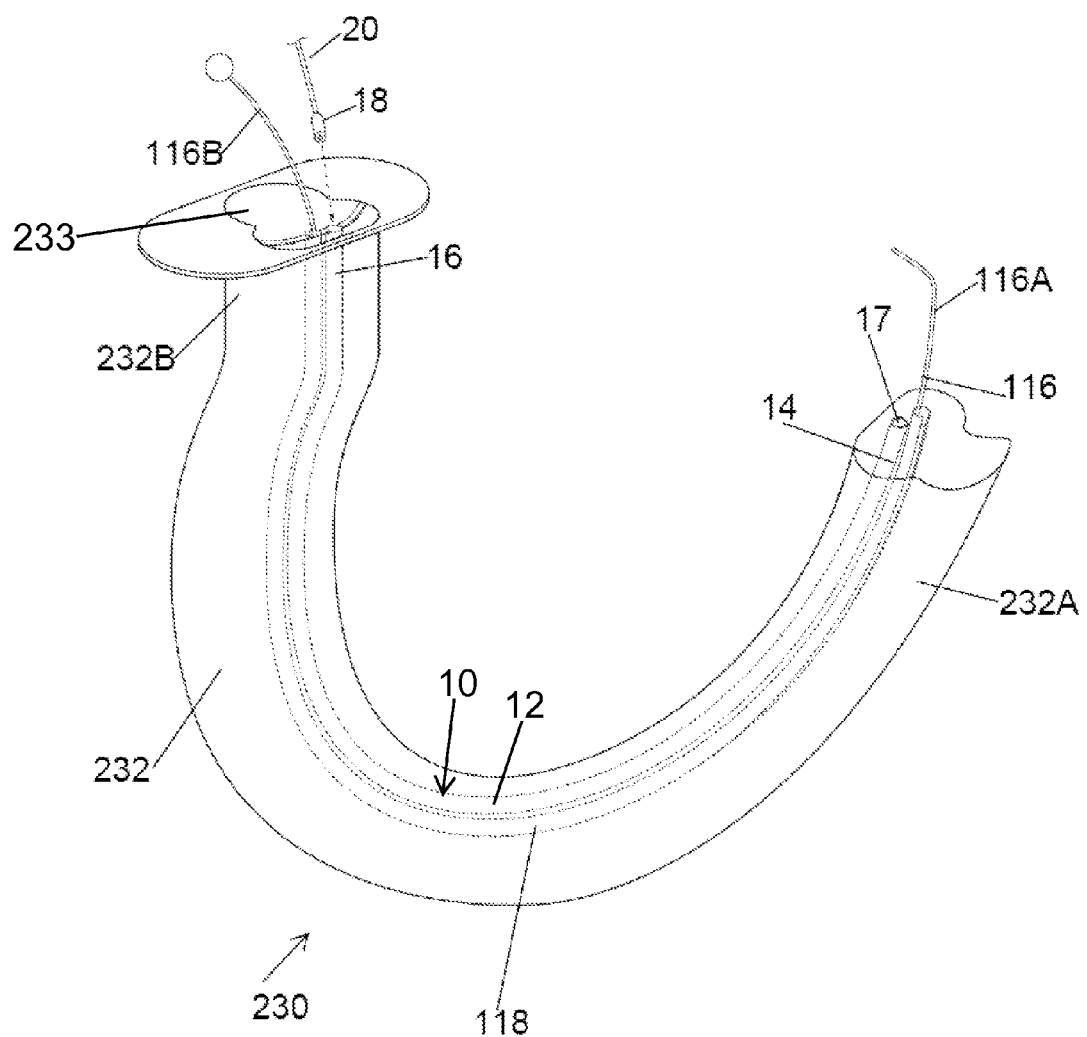

Further embodiments provide various oral airways as shown in FIGS. 16A, 16B, 16C, and 16D. Referring to FIG. 16A, an oral airway with a visualization device, generally 230, comprises a tubal body 232 with a lumen 233. The tubal body is slightly curved in a hook-like shape along the proximal-distal (232B-232A) axis. A visualization device 10 is placed inside of the lumen 233 of the tubal body 232. The visualization device 10 comprises a camera tube 12 and a camera 18. The camera tube 12 may be sealed or otherwise attached internally to the tubal body 232 inside of the lumen 233 and along the proximal-distal (232B-232A) axis. The camera tube 12 has a proximal end 16 and a distal end 14. The distal end 14 is in close proximity with the distal end 232A of the tubal body 232. The distal end 14 is sealed with a transparent material 17.

The camera tube 12 has an opening at the proximal end 16 through which the camera 18 is inserted into the camera tube 12 all the way to the distal end 14. The camera 18 communicates with a monitoring device either wirelessly or by electrical wire 20. The embodiment shown in FIG. 16B is the same as in FIG. 16A, except a light source 21 is added to the visualization device 10. The light source 21 may remain outside of the camera tube 12 or it may be built in the camera tube 12 or it may be a part of the camera 18.

The embodiment shown in FIG. 16C is the same as that of the FIG. 16A, except two whistles 234A and 234B are added inside of the lumen 233 of the tubal body 232. The whistle 234B is located at the proximal end of the tubal body 232 and it produces a sound when a patient breathes in. The whistle 234A is located at the distal end of the tubal body 232 and it produces a sound when the patient breathes out.

Further embodiments include an oral airway as shown in FIGS. 16A-16C, but further equipped with a sound and temperature monitoring device which is also placed inside of the lumen 233 and transmits information to a monitoring device which can be positioned at a remote location.

The embodiment of FIG. 16D is an intubating airway device with a visualization device, generally 230. The intubating airway device 230 comprises a tubal body 232 with a lumen 233 in which an endotracheal tube can be placed. A visualization device 10 comprises a camera tube 12 with a distal end 14 and a proximal end 16. The distal end 14 is sealed with a transparent material 17. A camera 18 is placed inside of the camera tube 12 through an opening at the proximal end 16. The camera tube 12 is placed inside the lumen 233 of the tubal body 232.

A bougie 116 is added inside of the tubal body 232 such that the bougie 116 is inserted in a tube 118 which shares the lumen with the lumen 233 along the proximal-distal (232B-232A) axis. A portion 116A of the bougie 116 protrudes outside the distal end 232A of the tubal body 232. A portion 116B of the bougie 116 protrudes outside the tubal body 232 from the proximal end 232B and over vocal cords. An endontracheal tube can be positioned inside the lumen 233 and the bougie 116 is used under constant visualization from the camera 10 to guide the placement of the endotracheal tube through patient's vocal cords. The distal end 14 of the camera tube 12 is in proximity with the distal portion 116A of the bougie 116 and therefore, the guided placement takes place under constant visualization.

Figure 17A:
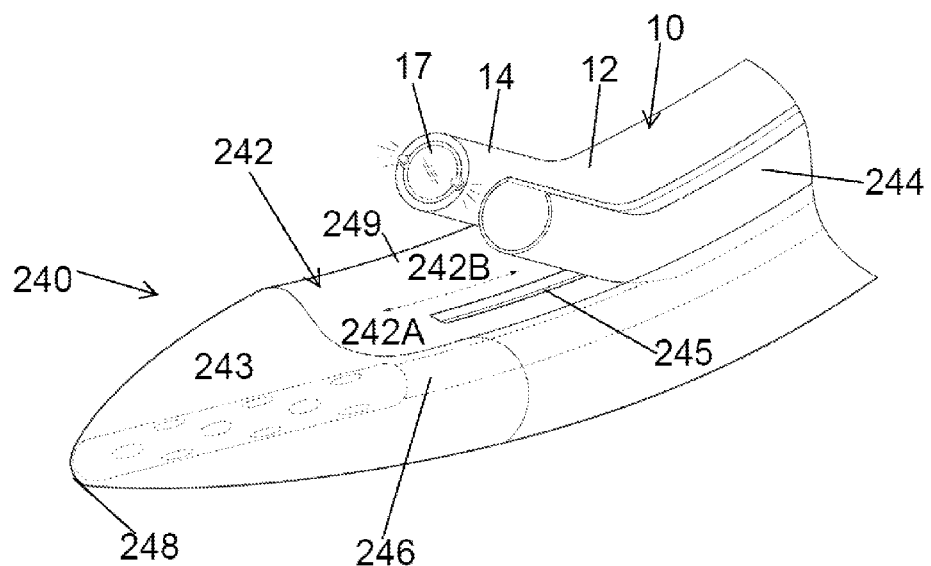
FIGS. 17A and 17B depict a side view for an esaphageal stethoscope equipped with a visualization device and working tube and bougie tube.

Further embodiments provide an esophageal stethoscope with a visualization device. Referring to FIG. 17A, it depicts an esophageal stethoscope with a visualization device, generally 240. It comprises a body 242 with a lumen 243 into which a sound-monitoring device 246 is placed. The body 242 may have a cylinder-like shape tapered at the distal end, and with the distal end the body 242 protruding with a tongue-like tip 248. At least a portion of the body 242 surface is slightly curved toward the lumen 243 and creates a surface 249. The visualization device, generally 10, comprises a camera tube 12 with a distal end 14 which is sealed with a transparent material 17, and a camera 18 which is placed inside of the camera tube 12 through an opening at the proximal end of the camera tube 12. The camera tube is positioned externally on surface 249 along the distal-proximal axis of the body 242. The camera tube 12 is connected with the surface 249 by a sliding means 245 such that the camera tube 12 can slide along the 242A-242B axis on the surface 249.

The camera 18 is placed inside of the camera tube 12 and because the camera tube 12 is sealed at the distal end 14, the camera 18 does not come in contact with a patient and the camera 18 does not need to be sterilized and it can be reused in other applications. The camera 18 is connected by electric wire 20 or wirelessly to a monitoring device. The camera 18 is not disposable and can be reused in other applications.

Figure 17B:
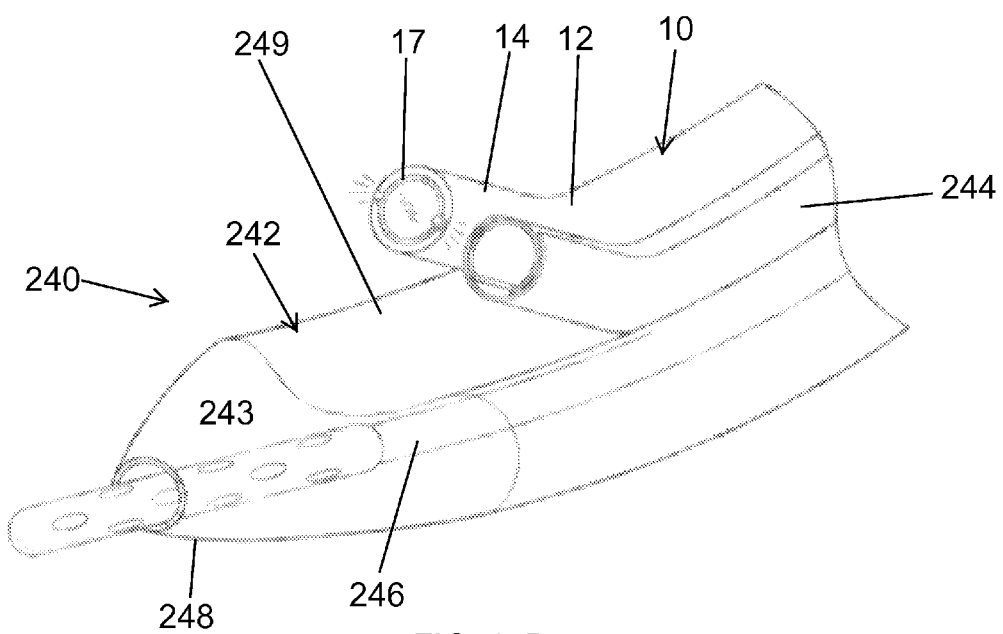

The stethoscope 240 is further equipped with a bougie tube 244 which is also located on the surface 249 and is connected to the surface 249 with a sliding means 245 such that the bougie tube 244 can slide along the 242A-242B axis. FIG. 17B provides an alternative embodiment for the stethoscope 240, in which the sound and temperature monitoring device 246 can protrude through an opening at the 248 tip.

Figure 18A:
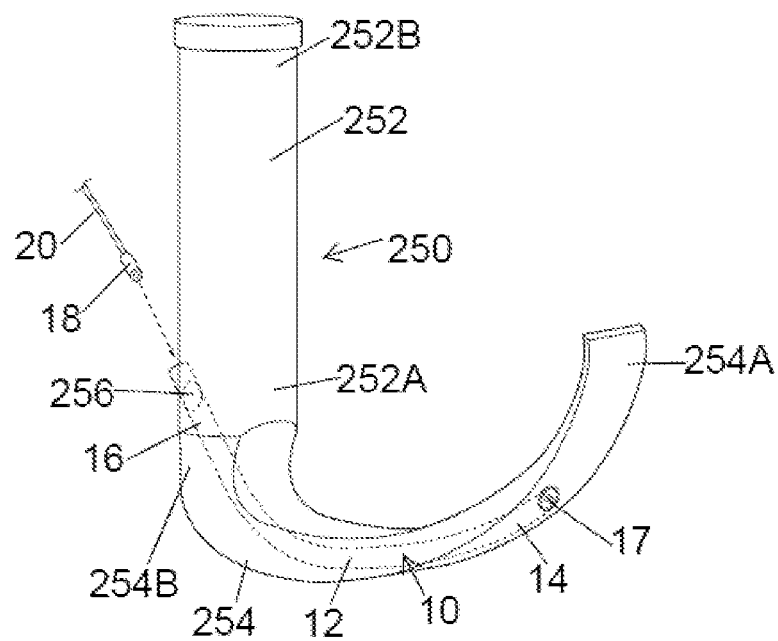
FIGS. 18A-18B depict a side view for a one-piece laryngoscope with a visualization device.
Figure 18B:
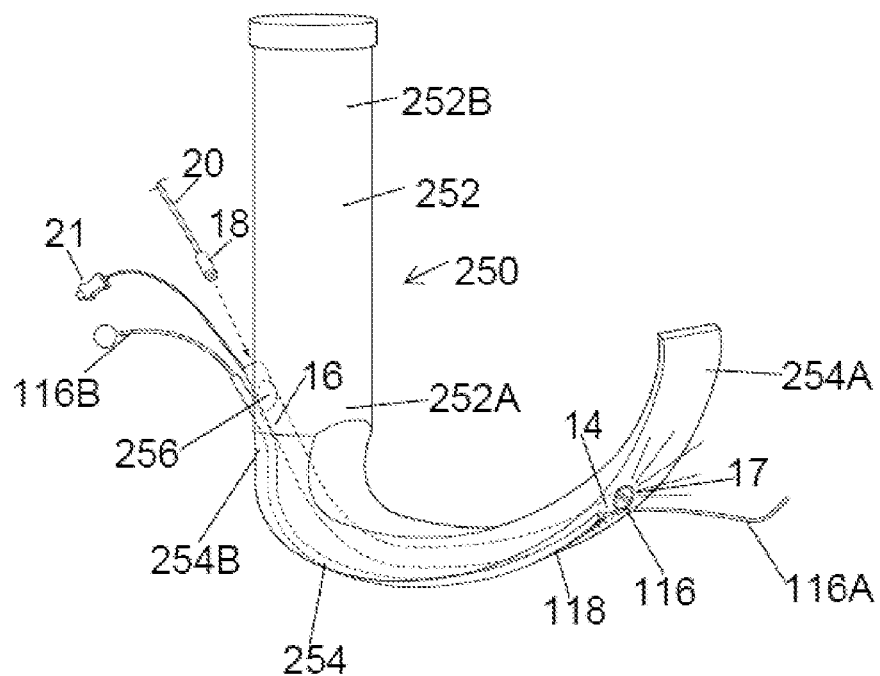

A further embodiment provides a one-piece video-laryngoscope with a visualization device, generally 250, as shown in FIGS. 18A and 18B. The video-laryngoscope 250 comprises a tubal body 252 which has a proximal end 252B and a distal end 252A. The tubal body 252 extends with a scoop-like portion 254 at the distal end 252A. The scoop-like portion 254 curves horizontally such that the distal end 254A of the scoop-like portion 254 is nearly parallel to the proximal end 254B of the scoop-like portion. The tubal body 252 has an opening 256 near its distal end 252A. A visualization device 10 which comprises a camera 18 placed inside of a camera tube 12 is placed through the opening 256 such that the distal end 14 of the camera tube 12 may be in proximity with the proximal end 254A of the scoop-like portion 254. The device can be easily inserted to an upper esophagus and visualize vocal cords.

However, the position of the distal end 14 can be adjusted as needed by sliding the camera tube 12 through the opening

256. The distal end 14 is sealed with a transparent material 17 such that the camera 18 does not come in contact with a patient's body and therefore, the camera 18 does not need to be sterilized and it can be reused in multiple applications. The camera 18 is inserted into the camera tube 12 through an opening at the proximal end 16. The camera 18 is connected to at least one monitoring device either by electrical wire 20 or wirelessly.

The embodiment of FIG. 18B is the same as that of FIG. 18A, except a light source 21 is added to the visualization device 10 as described in connection with the light source 21 in other medical devices above. A bougie 116 in a tube 118 is also added through the opening 256, and the distal end 116A of the bougie 116 can be manipulated at the proximal end 116B such that the placement of the device 250 is guided under continuous visualization with the camera 18.

Figure 19:
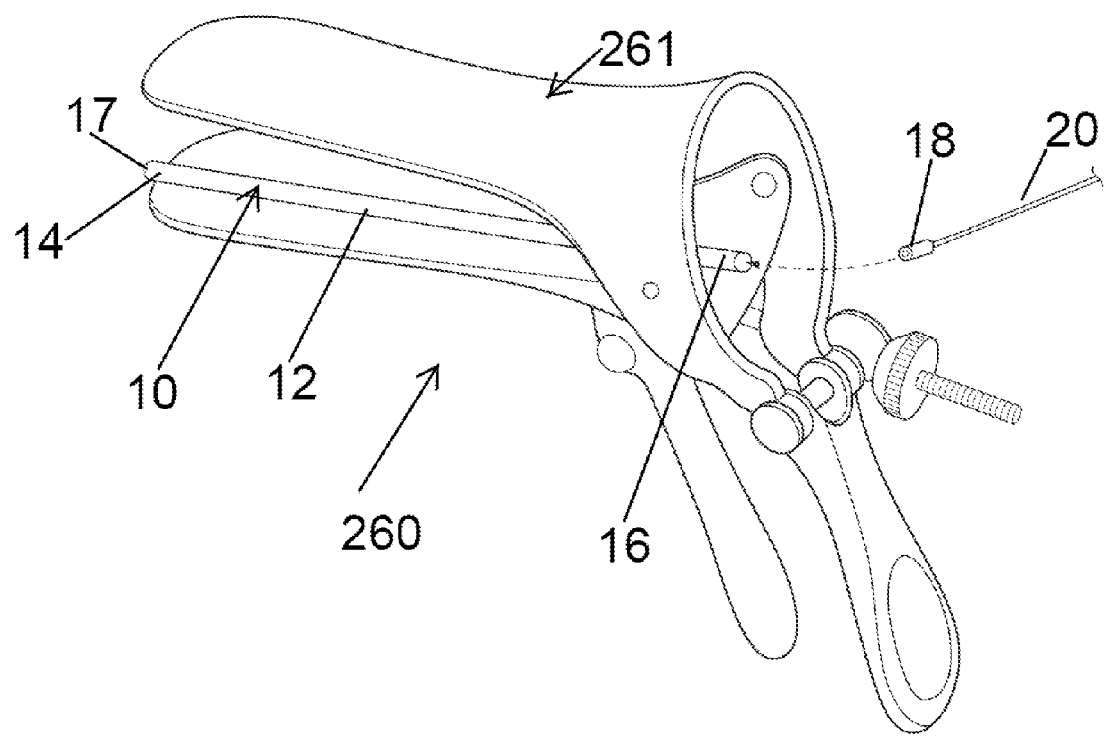
FIG. 19 depicts a side view of a speculum with a visualization device.

A further embodiment includes a vaginal speculum with visualization device, generally 260 as shown in FIG. 19. Any speculum 261, including disposable, generally known and used for a pelvic exam can be equipped with a visualization device, generally 10, which comprises a camera 18 placed inside of a camera tube 12. The camera tube 12 can be attached to the speculum 261 or to some other instrument. The camera 18 is placed in the camera tube 12 through an opening at a proximal end 16 and is moved all the way toward the distal end 14 which is sealed with a transparent material 17. The camera 18 connected to at least one monitoring device by electric wire 20 or the camera 18 can be connected wirelessly.

Further embodiments relate to various tubing equipped with a visualization device shown in FIG. 1A and as described in more detail below.

Figure 20A:
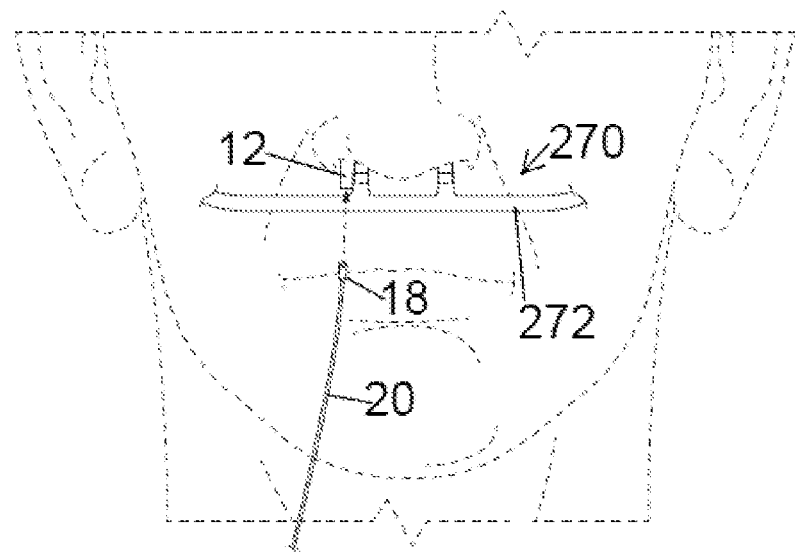
FIG. 20A-F depict a nasal cannula with a visualization device.

FIGS. 20A-20F refer to various embodiments for a nasal cannula with a visualization device, generally 270. FIG. 20A shows the positioning of a nasal cannula 272 on patient's head with a visualization device 10 added to one of the two nostril tubes. The nasal cannula 272 can be any nasal cannula known in the art and used by medical practitioners. The visualization device 10 is as described in connection with FIG. 1A and comprises a camera 18 inserted inside of a camera tube 12. The camera tube 12 is sealed or otherwise attached externally along at least one nostril tube 274 of the nasal cannula 272 as shown in more detail in FIG. 20C. This nasal cannula with the visualization device 10 provides continuous visualization of vocal cords, upper esophagus. The cannula can be used to determine whether vocal cords are moving correctly, if there is any abnormal anatomy and the color of the patient's tissues.

Figure 20B:
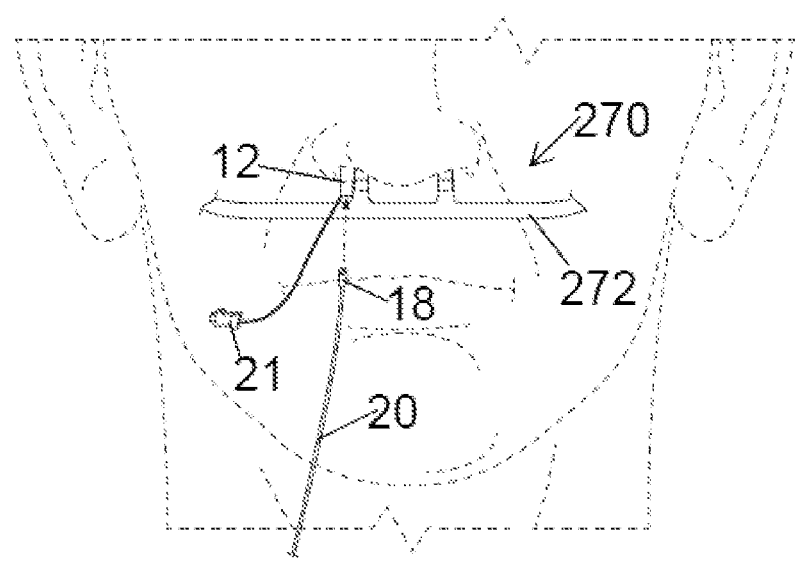
Figure 20C:
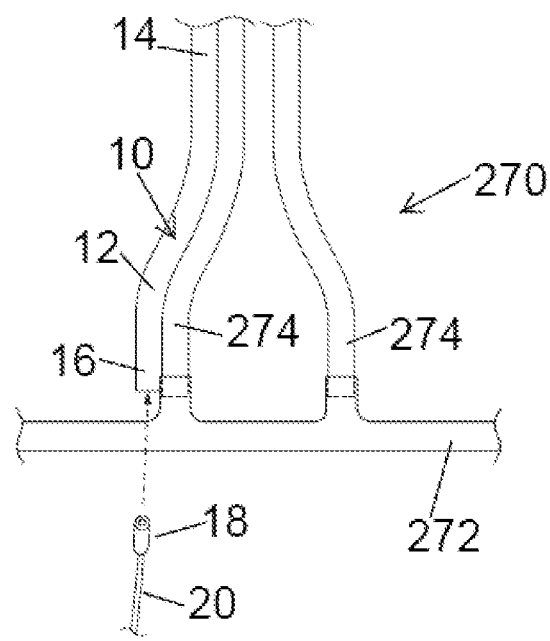
Figure 20D:
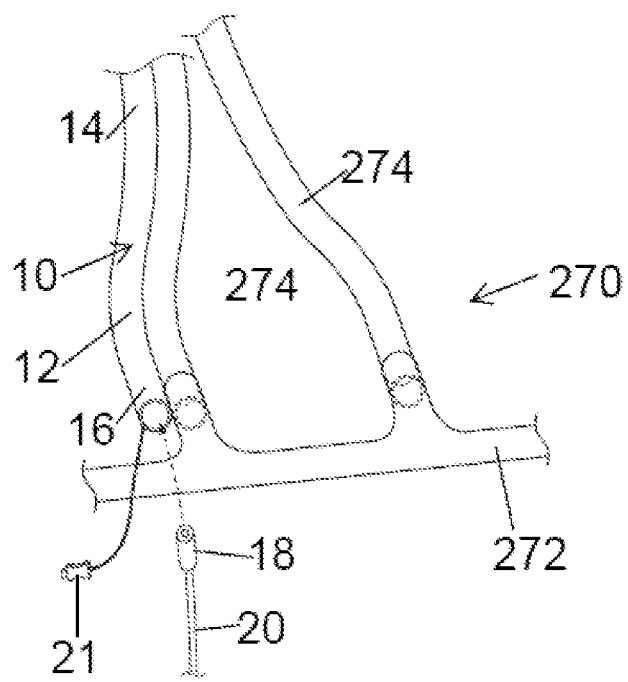
Figure 20E:
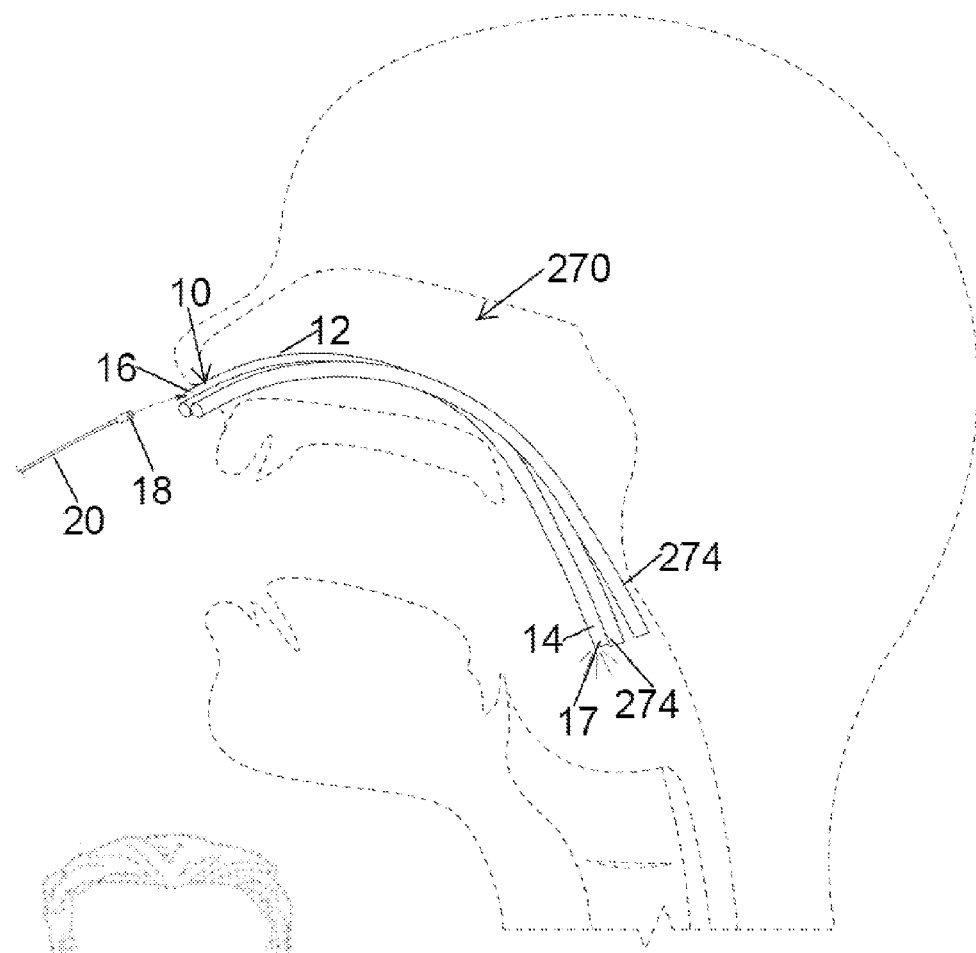
Figure 20F:
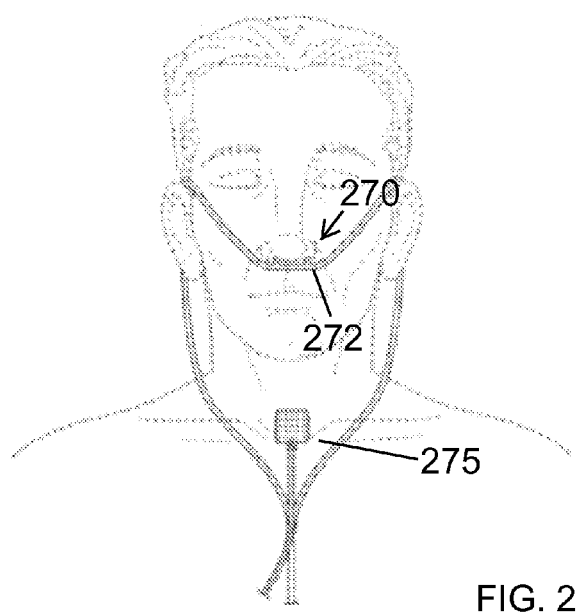

As shown in FIG. 20E, the nasal cannula with the visualization device can be properly positioned through patient's nostrils as the positioning is guided and constantly visualized with the camera device 10. The distal end 14 of the camera tube 12 aligns with the distal end of at least one nostril tube 274. As shown in FIG. 20F, the nasal cannula with the visualization device can be further equipped with an external stethoscope 275, which can be placed on patient's chest externally and monitors breathing and heart-beat sounds.

FIGS. 20B and 20D show the same embodiment as in FIGS. 20A and 20C, except the visualization device 10 is equipped with a light source 21 as was described in connection with the light source 21 in other embodiments.

Figure 21:
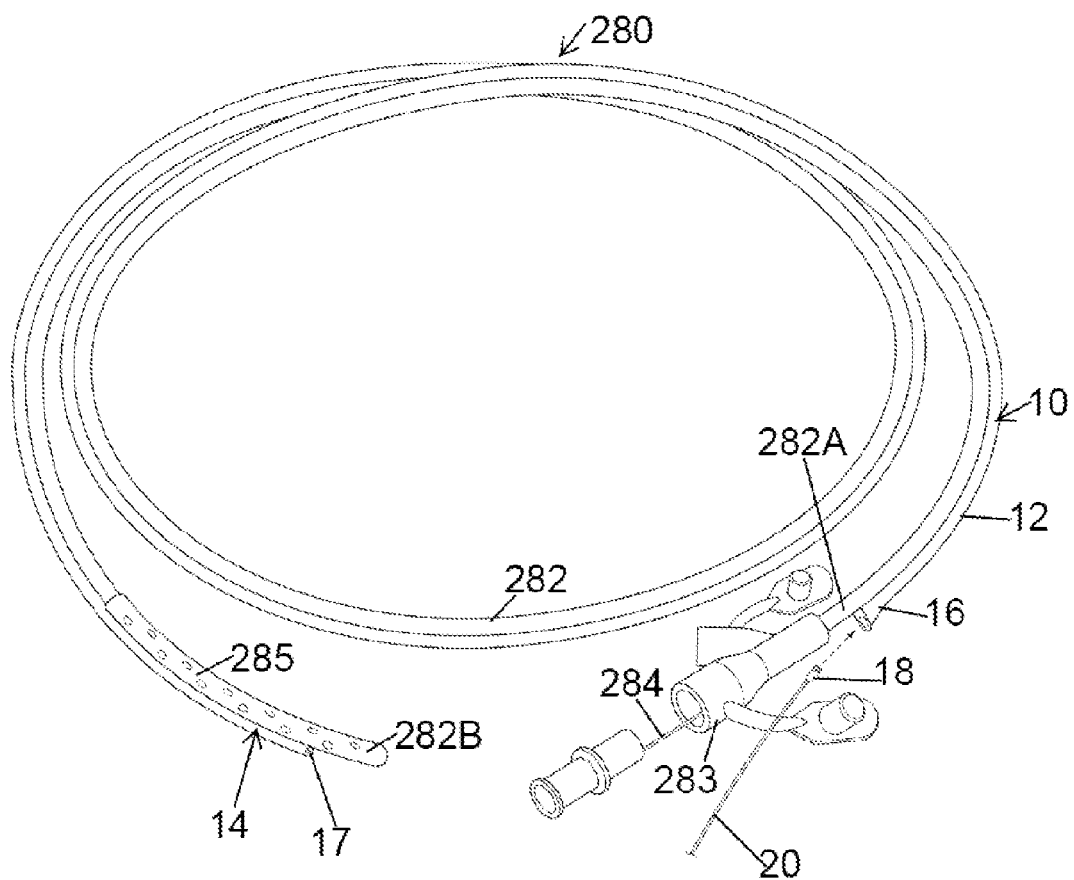
FIG. 21 is a feeding tube equipped with a visualization device.

A further embodiment includes a feeding tube with a visualization device, generally 280, as shown in FIG. 21. A visualization device, generally 10, is sealed or otherwise attached externally along the proximal-distal (282A-282B) axis of a feeding tube 282. The visualization device 10 is essentially the same as described in connection with FIG. 1A and other embodiments above. It comprises a camera tube 12 with a proximal end 16 and a distal end 14. A camera 18 with wire 20 is inserted into the camera tube 12 through an opening at the proximal end 16 and is slid all the way to the distal end 14 which is sealed with a transparent material 17. The camera 18 does not come in contact with a patient's body and can be reused in multiple devices. Any feeding tubes known in the art can be used in this embodiment, including a feeding tube with a stylet 284 as shown in FIG. 21. The feeding tube 282 can be equipped with an adaptor 283 at the proximal end 282A. The feeding tube 282 may further comprise a plurality of holes 285 at the distal end 282B for food distribution.

Figure 22A:
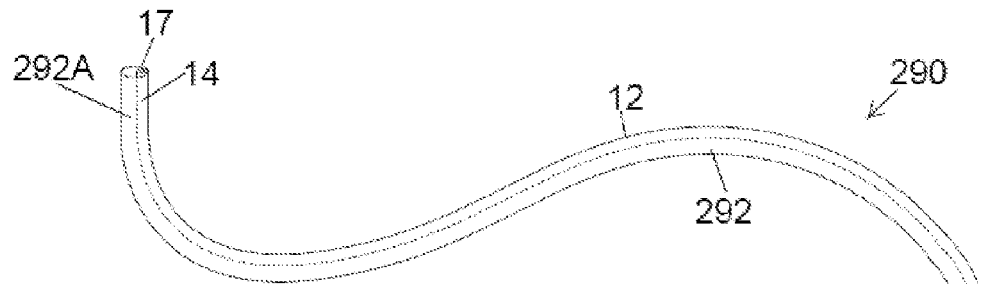
FIG. 22A, 22B, 22C depict various embodiments of a suction tube equipped with a visualization device.
Figure 22B:
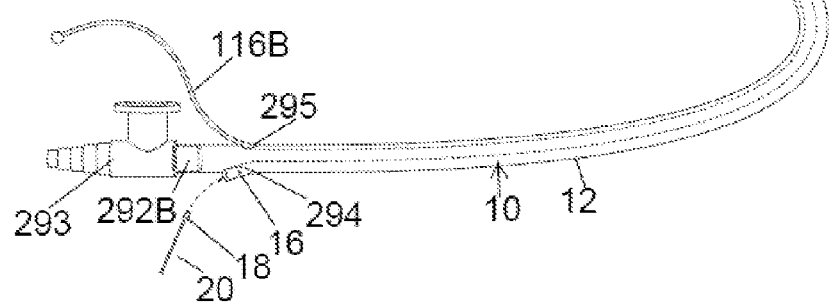
Figure 22C:
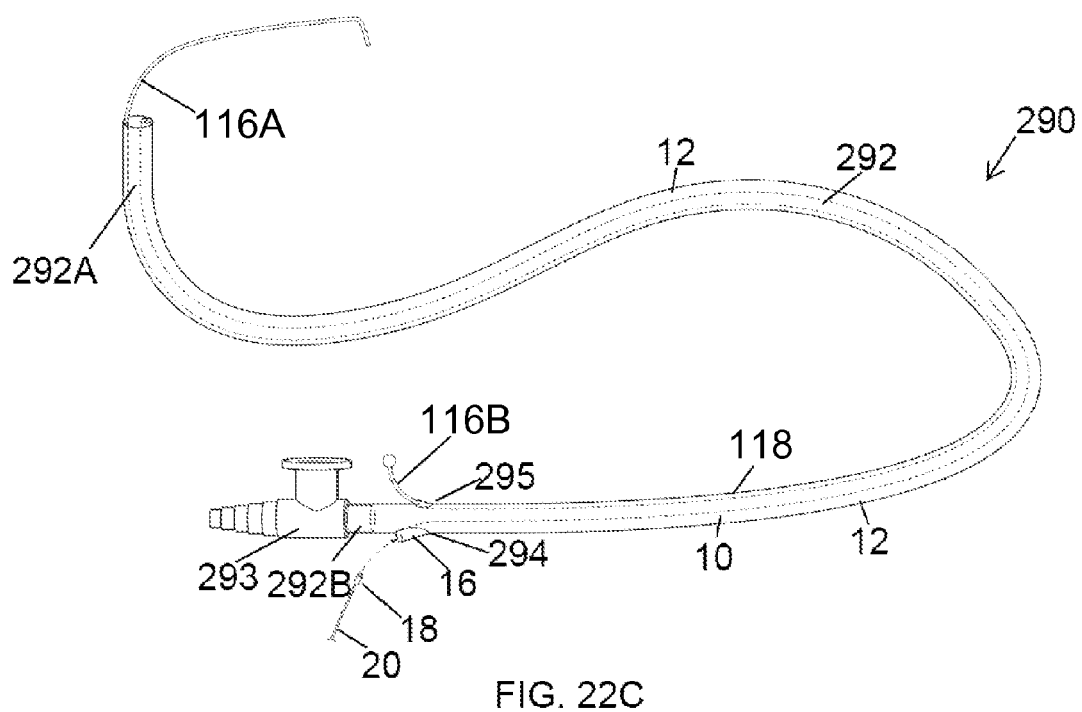

Further embodiments provide various suction tubes equipped with a visualization device, generally 290, as shown in FIGS. 22A, 22B and 22C. Any suction tube including but not limited to the nasal gastric tubes known in the art can be used and in general a suction tube 292 with an adaptor 293 at a proximal end 292B is suitable, as shown in FIG. 22A. A visualization device, generally 10, comprises a camera tube 12 and a camera 18 with wire 20. The camera 18 is inserted into the camera tube 12 through an opening at a proximal end 16 and is slid all the way to the distal end 14 of the camera tube 12. The distal end 14 is sealed with a transparent material 17. The camera 18 can transmit information to a remote location.

The camera tube 12 is placed inside of the suction tube 292 through an opening 294 at the proximal end 292B of the suction tube 292. The camera tube 12 is then aligned with the length of the suction tube 292 such that the distal end 14 of the camera tube 12 is in close proximity with the distal end 292A of the suction tube 292.

FIGS. 22B and 22C is a further embodiment of a suction tube with a visualization device, generally 290 as shown in FIG. 22A, but it is further equipped with a bougie 116 placed inside of a tube 118 which is placed inside of the suction tube 292 through an opening 295. A distal end 116A of the bougie 116 can protrude outside the distal end 292A of the suction tube 292 and can be manipulated by a medical practitioner with a proximal end 116B which protrudes outside a patient such as the placement of the suction tube 292 is guided under constant visualization with the camera 18 through the distal end 14 of the camera tube 12. The bougie 116 under constant visualization from the camera 12 permits rapid and accurate placement of the device 290 in a patient. The bougie 116 can be used to guide the placement of the device 290 and moving it left or right in the trachea.

Figure 23:
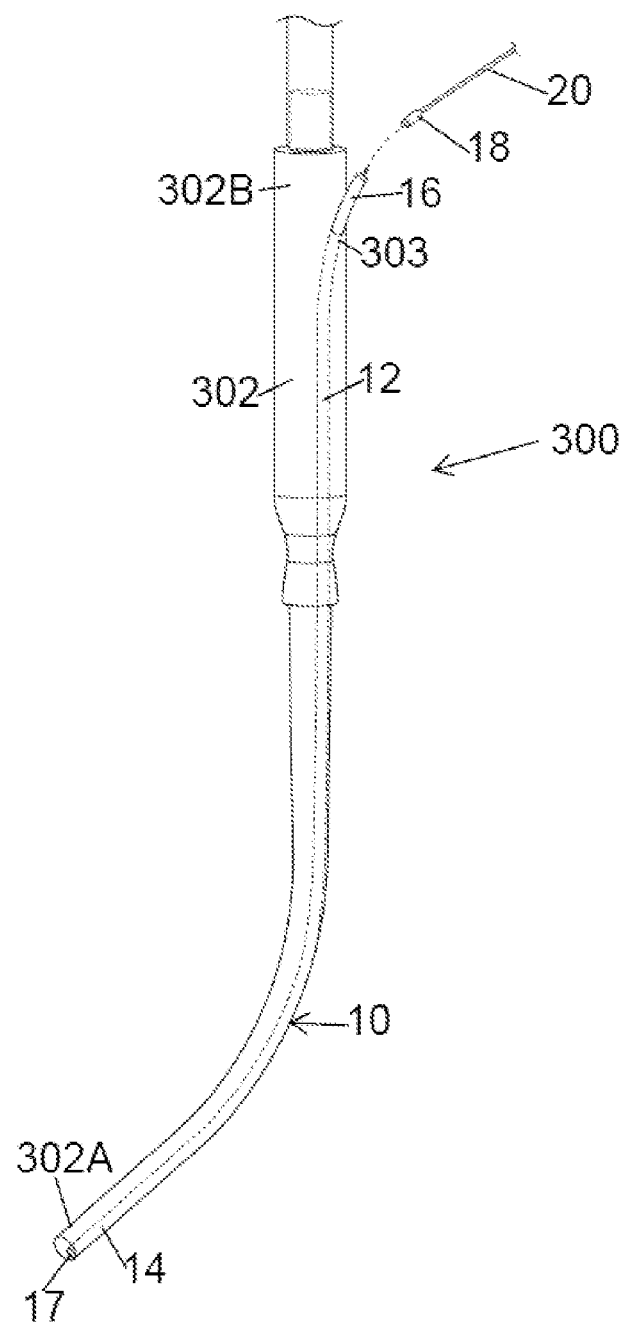
FIG. 23 depicts a suction catheter equipped with a visualization device.

Referring to FIG. 23, this embodiment provides a suction catheter with a visualization device, generally 300. The suction catheter 302 is not flexible and can be any suction catheter known in the art. A visualization device, generally 10, is positioned inside the suction catheter 302 through an opening 303 which is in near proximity with a proximal end 302B of the suction catheter 302. The visualization device 10 comprises a camera 18 with wire 20 which is placed inside of a camera tube 12 through an opening at a proximal end 16 of the camera tube 12 and then the camera 18 is slid to the distal end 14 which is sealed with a transparent material 17. The distal end 14 of the camera tube 12 is aligned with the distal end 302A of the suction catheter 302, while the proximal end 16 of the camera tube 12 protrudes outside the patient's body such as the camera 18 can be pulled out from the camera tube 12 as needed. In other embodiments, the suction tube is placed externally and this combination can work with suction caps.

Figure 24:
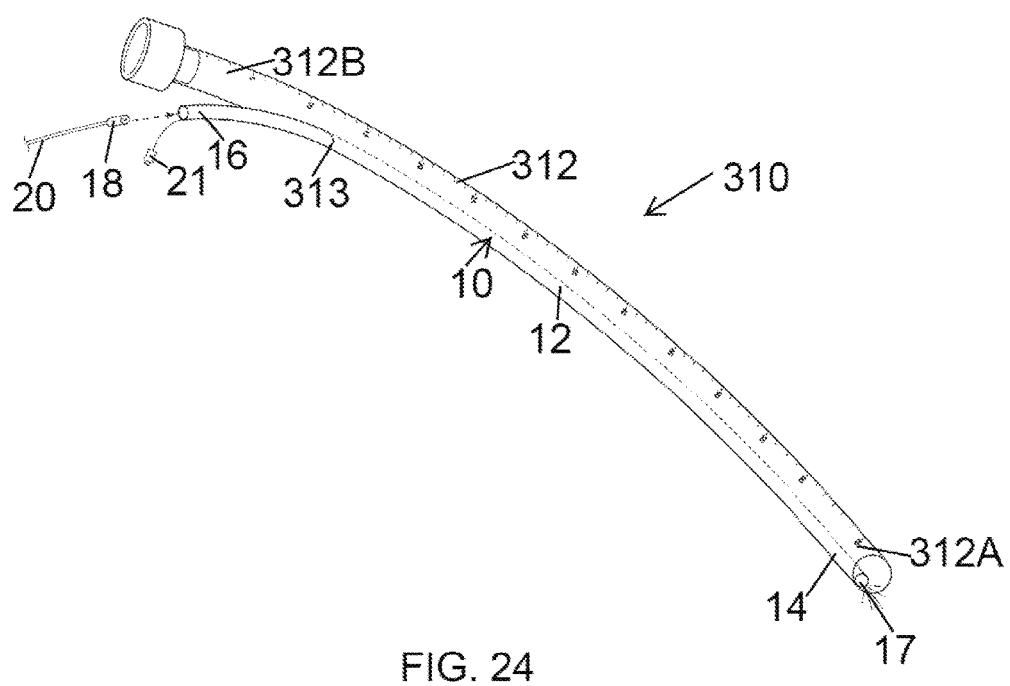
FIG. 24 depicts an endotracheal changing tube equipped with a visualization device.

Referring to FIG. 24, this embodiment provides an endotracheal changing tube with a visualization device, generally 310. An endotracheal changing tube can be any endotracheal changing tube as known in the art. A visualization device, generally 10, comprises a camera 18 with wire 20 which is placed inside of a camera tube 12 through an opening at a proximal end 16 of the camera tube 12 and slid all the way to a distal end 14 of the camera tube 12. The distal end 14 is sealed with a transparent material 17. The visualization device 10 is placed inside of the endotracheal changing tube 312 through an opening 313 in the changing tube 312 such as the camera tube 12 is aligned with the changing tube 312 along the proximal-distal (312B-312A) axis, and the distal end 14 of the camera tube 12 is in close proximity with the distal end 312A of the changing tube 312. In other embodiments, the camera tube 12 can be placed outside of the endotracheal changing tube or it can be fitted externally onto an endotracheal changing tube known in the art.

While certain medical devices are described above, a person of skill would appreciate that this invention also includes embodiments with various obvious modifications as would be easily apparent to a person of skill.

What is claimed is:

1. A medical device for intubating a patient, the medical device comprising a medical visualization device, the medical visualization device comprising:
    a camera tube, the camera tube comprising a distal end and a proximal end, wherein the distal end is sealed with a transparent material and a proximal end has an opening; and
    a camera with a wire placed inside of the camera tube, wherein the camera can be placed inside of the camera tube and it can be retracted from the camera tube on demand while the camera tube remains inserted in the patient, and wherein the camera can be reused in various devices without sterilization and wherein the camera can transmit images to a remote location wirelessly;
    wherein the camera tube of the medical visualization device is sealed to, attached to or otherwise combined with at least one of the following second devices: an endotracheal tube, a supraglottic airway device, a ventilator adaptive cap, a dilator, a tracheostomy device, a nasal trumpet, an oral airway, an esophageal stethoscope, a stylet, a bougie, a speculum, a nasal cannula, a feeding tube, a suction tube, a suction catheter, and an endotracheal changing tube.

2. The medical visualization device of claim 1, wherein the camera tube comprises a fiber optic material.

3. The medical visualization device of claim 1, wherein the device can transmit information wirelessly and wherein the device is further equipped with at least one of the following: a light source, a stylet, a sound and temperature monitoring device, suction tube, bougie tube, stylet tube and a tool tube.

4. The medical visualization device of claim 1, wherein the camera is a digital camera.

5. The medical visualization device of claim 1, wherein the visualization device is in communication with at least one monitoring device wirelessly.

6. A method of continuous monitoring of a patient's at least one internal organ, the method comprising placing in the patient the visualization device of claim 1, transmitting images of the internal organ in real time with the camera through the transparent material at the distal end of the camera tube, and analyzing the transmitted images.

7. The method of claim 6, wherein the images, sound, data, information about temperature are transmitted wirelessly, broadcast or recorded to at least one device positioned at a remote location.

8. The method of claim 6, wherein the internal organ is selected from at least one of the following: nasopharynx, pharynx, hypo pharynx, supraglottic structures, subglottic airway, vocal cords, thorax, stomach and vagina.

9. The visualization device of claim 1, wherein the length of the camera tube can be adjusted to the length of at least one of the following second devices by sliding: an endotracheal tube, a supraglottic airway, airway device, oral airway, dilator, tracheostomy device, intubating oral airway, esophageal stethoscope, nasal cannula, feeding tube, stylet, bougie, suction tube and endotracheal changing tube and wherein the camera tube can slide along the distal/proximal axis of the device.

10. A method for placing a medical device in a patient, the method comprising equipping the medical device with the visualization device of claim 1 and a bougie and guiding the placement of the device with the bougie under continuous visualization with the visualization device of claim 1.

11. The medical device of claim 1 which further comprises at least one of the following a bougie and a sound- and temperature-monitoring device.

12. The medical device of claim 1 wherein the camera is retractable from the device and reusable in other devices.

13. The medical device of claim 1, wherein the camera tube of the visualization device is sealed, attached or otherwise connected externally to the second device.

14. The medical device of claim 1, wherein the visualization device is equipped with a light source.

15. The medical device of claim 1, wherein the second device is an endotracheal tube selected from the group consisting of: an endotracheal tube which comprises a sleeve through which the visualization device can be inserted, an endotracheal tube into which the visualization device is placed internally through a ventilator adaptive cap and an endotracheal tube to which the visualization device is attached.

16. The medical device of claim 1, wherein the second device is the supraglottic airway device or airway device.

17. The medical device of claim 1, wherein the visualization device is combined with the ventilator adaptive cap by being inserted through the cap.

18. The medical device of claim 1, wherein the second device is an endotracheal tube and wherein the visualization device is placed inside of the endotracheal tube through an opening on one side of the endotracheal tube, and wherein a plastic sleeve being attached over the opening such that the sleeve can slide up and down and facilitates keeping the visualization device sterile while it is moved in and out of the endotracheal tube.

19. The medical device of claim 1, wherein the second device is an endotracheal tube, and wherein the visualization device being positioned externally on the endotracheal tube along the proximal-distal axis of the endotracheal tube, and wherein a plastic sleeve being attached to the endotracheal tube such that the sleeve can slide up and down outside the endotracheal tube and facilitates the movement of the visualization device along the proximal-distal axis of the endotracheal tube.

20. The medical device of claim 19, wherein the endotracheal tube is equipped with a cuff wrapped around the endotracheal tube near its distal end; and wherein the visualization device can slide outside the endotracheal tube along the proximal-distal axis such that the visualization device can be proximal or distal to the cuff.

21. The medical device of claim 1, wherein the visualization device is equipped with at least one ring, the visualization device is positioned externally on the second device along the proximal-distal axis of the second device, and the visualization device is connected to the second device with the at least one ring, and wherein the visualization device can slide along the proximal-distal axis of the second device.

22. The medical device of claim 1, wherein the second device is an oral airway which comprises a tubal body with a lumen, the tubal body is slightly curved in a hook-like shape and the visualization device is placed inside of the lumen and the visualization device can slide inside of the lumen along the proximal-distal axis of the oral airway.

* * * * *